US009512156B2

(12) United States Patent
Zobi et al.

(10) Patent No.: US 9,512,156 B2
(45) Date of Patent: Dec. 6, 2016

(54) CARBON MONOXIDE RELEASING RHENIUM COMPOUNDS FOR MEDICAL USE

(75) Inventors: Fabio Zobi, Zürich (CH); Roger Alberto, Winterthur (CH); Lukas Kromer, Winterthur (CH)

(73) Assignee: UNIVERSITY OF ZURICH, Zurich (CH)

( * ) Notice: Subject to any disclaimer, the term of this patent is extended or adjusted under 35 U.S.C. 154(b) by 19 days.

(21) Appl. No.: 13/583,390

(22) PCT Filed: Mar. 4, 2011

(86) PCT No.: PCT/EP2011/001077
§ 371 (c)(1),
(2), (4) Date: Sep. 7, 2012

(87) PCT Pub. No.: WO2011/110315
PCT Pub. Date: Sep. 15, 2011

(65) Prior Publication Data
US 2012/0328712 A1 Dec. 27, 2012

(30) Foreign Application Priority Data
Mar. 8, 2010 (EP) .................... 10002342

(51) Int. Cl.
| *A61K 31/55* | (2006.01) |
| *A61K 31/714* | (2006.01) |
| *A61K 33/24* | (2006.01) |
| *C01G 47/00* | (2006.01) |
| *C07F 13/00* | (2006.01) |
| *C07H 23/00* | (2006.01) |
| *A61P 9/00* | (2006.01) |
| *A61P 9/10* | (2006.01) |
| *A61P 29/00* | (2006.01) |
| *A61P 7/02* | (2006.01) |
| *A61P 35/00* | (2006.01) |
| *A61P 15/00* | (2006.01) |
| *A61P 11/00* | (2006.01) |
| *A61P 9/12* | (2006.01) |
| *A61P 11/06* | (2006.01) |
| *A61P 25/00* | (2006.01) |
| *A61P 13/12* | (2006.01) |
| *A61P 1/16* | (2006.01) |

(52) U.S. Cl.
CPC ............ *C07F 13/00* (2013.01); *C07F 13/005* (2013.01)

(58) Field of Classification Search
CPC ...... A61K 31/714; A61K 33/24; A61P 9/10; C07F 13/005; C07F 13/00; C07F 9/5027; C07F 15/004; C07F 15/0053; C07F 15/0066; C07F 15/008; C07F 5/025; C07F 9/5068; C07F 9/5072
See application file for complete search history.

(56) References Cited

U.S. PATENT DOCUMENTS

| 2004/0067261 A1 | 4/2004 | Haas et al. |
| 2006/0148900 A1 | 7/2006 | Haas et al. |
| 2006/0233890 A1 | 10/2006 | Haas et al. |
| 2007/0207217 A1 | 9/2007 | Haas et al. |
| 2007/0207993 A1 | 9/2007 | Haas et al. |

FOREIGN PATENT DOCUMENTS

| WO | WO 02/092075 | 11/2002 |
| WO | WO 2005/013691 | 2/2005 |
| WO | WO 2009/013612 | 1/2009 |

OTHER PUBLICATIONS

Zobi Angew Chem Int. Ed 2004.*
Drew, M. et al. "Phosphine Containing Rhenium(III) Carbonyl Complexes. The Crystal and Molecular Structure of Tribromodicarbonylbis(Dimethylphenylphosphine) Rhenium(III)" *Polyhedron*, 1984, pp. 1059-1063, vol. 3, No. 9/10.
Zingales, F. et al. "Halogen-Bridged Rhenium Carbonyl Nitrosyl Complexes and Derivatives" *Inorganic Chemistry*, 1971, pp. 507-510, vol. 10, No. 3.
Kromer, L. et al. "Substitution reactions with [ReBr$_2$(CO)$_2$(NCCH$_3$)2]": a convenient route to complexes with the cis-[Re(CO)$_2$]$^+$ core *Dalton Transactions*, 2008, pp. 5800-5806.
Zobi, F. et al. "Synthesis and Reactivity of the 17 e$^-$ Complex [Re$^{II}$Br$_4$(CO)$_2$]$^{2-}$: A Convenient Entry into Rhenium(II) Chemistry" *Inorganic Chemistry*, 2009, pp. 8965-8970, vol. 48.
Zobi, F. et al. "CO Releasing Properties and Cytoprotective Effect of cis-trans[Re$^{II}$(CO)$_2$Br$_2$L$_2$]n Complexes" *Inorganic Chemistry*, 2010, pp. 7313-7322, vol. 49.
Motterlini, R. et al. "Carbon Monoxide-Releasing Molecules : Characterization of Biochemical and Vascular" *Circulation Research*, 2002, pp. 17-24.
Foresti, R. et al. "Use of carbon monoxide as a therapeutic agent: promises and challenges" *Intensive Care Medicine*, 2008, pp. 649-658, vol. 34.
Motterlini, R. et al. "Therapeutic applications of carbon monoxide-releasing molecules" *Expert Opinion on Investigational Drugs*, 2005, pp. 1305-1318, vol. 14, No. 11.
Motterlini, R. et al. "Bioactivity and Pharmacological Actions of Carbon Monoxide-Releasing Molecules" *Current Pharmaceutical Design*, 2003, pp. 2525-2539, vol. 9.

(Continued)

*Primary Examiner* — Suzanne Ziska
*Assistant Examiner* — Thurman Wheeler
(74) *Attorney, Agent, or Firm* — Saliwanchik, Lloyd & Eisenschenk

(57) ABSTRACT

The present invention relates to new rhenium compounds of formula (I)

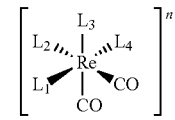

with medical utility, corresponding pharmaceutical compositions as well as medical uses thereof.

4 Claims, 5 Drawing Sheets

(56) References Cited

OTHER PUBLICATIONS

Motterlini, R. et al. "CORM-A1: a new pharmacologically active carbon monoxide-releasing molecule" *The FASEB Journal*, Feb. 2005, pp. 284-286, vol. 19.

Johnson, T. R. et al. "Metal Carbonyls: A New Class of Pharmaceuticals?"*Angewandte Chemie Int. Ed.*, 2003, pp. 3722-3729, vol. 42.

Alberto, R. et al. "Synthesis and Reactivity of $[NEt_4]_2[ReBr_3(CO)_3]$. Formation and Structural Characterization of the Clusters $[NEt_4][Re_3(\mu_3-OH)(\mu-OH)_{3(CO)9}]$ and $[NEt_4] Re_2(\mu-OH)_3(CO)_6]$ by Alkaline Titration" *Journal of Chemical Society, Dalton Transactions*, 1994, pp. 2815-2820.

Abram, U. et al. "Darstellung und Strukturen von $(Et_4N)_2[Re(CO)_3(NCS)_3]$ und $(Et_4N) [Re(CO)_2Br_4]$" *Zeitschrift für anorganische und allgemeine Chemie*, 1996, pp. 813-818, vol. 622.

Clark, J. E. et al. "Cardioprotective Actions by a Water-Soluble Carbon Monoxide-Releasing Molecule" *Circulation Research*, 2003, pp. 2-8.

Zobi, F. et al. "Head-to-Head (HH) and Head-to-Tail (HT) Conformers of *cis*-Bis Guanine Ligands Bound to the $[Re(CO)_3]^{1+}$ Core" *Inorganic Chemistry*, 2004, pp. 2087-2096, vol. 43, No. 6.

Zobi, F. et al. "17 $e^-$ Rhenium Dicarbonyl CO-Releasing Molecules on a Cobalamin Scaffold for Biological Application" *Dalton Transactions*, 2011, pp. 1-36.

Motterlini, R. et al. "The therapeutic potential of carbon monoxide" *Nature*, Sep. 2010, pp. 728-743, vol. 9.

Romao, C. et al. "Developing drug molecules for therapy with carbon monoxide" *Chemical Society Reviews*, 2012, pp. 3571-3583, vol. 41.

Written Opinion in International Application No. PCT/EP2011/001077, Apr. 27, 2011, pp. 1-5.

Spingler, B. et al. "Interaction of Mono- and Dinuclear Metal Complexes with Mono—and Oligonucleotides for Analytical, Radio- and Chemotoxic Purposes" *CHIMIA*, 2005, pp. 826-831, vol. 59, No. 11.

Kottelat, E. et al. "Towards Cardiolite-Inspired Carbon Monoxide Releasing Molecules—Reactivity of $d^4$, $d^5$ Rhenium and $d^6$ Manganese Carbonyl Complexes with Isocyanide Ligands" *European Journal of Inorganic Chemistry*, 2015, vol. 34, pp. 5628-5638.

* cited by examiner

CARBON MONOXIDE RELEASING RHENIUM COMPOUNDS FOR MEDICAL USE

CROSS-REFERENCE TO RELATED APPLICATION

This application is the U.S. national stage application of International Patent Application No. PCT/EP2011/001077, filed Mar. 4, 2011.

FIELD OF THE INVENTION

The present invention relates to new rhenium compounds, preferably non-radioactive rhenium compounds for medical use, corresponding pharmaceutical compositions as well as medical uses thereof.

BACKGROUND OF THE INVENTION

In recent years carbon monoxide has been acknowledged as a fundamental small molecule messenger in mammals. The endogenous production of CO is associated with the heme metabolic pathway, in particular the action of a family of enzymes known as heme oxigenases, which catalyze the oxidation of heme to biliverdin and thereby liberate free iron and carbon monoxide. The tissue-specific distribution of heme oxigenases and, thus, the liberated carbon monoxide have been linked to several physiological effects. For example, carbon monoxide is a signaling molecule in the inducible defensive system against stressful stimuli; it has a fundamental role in the circulatory system by improving vasorelaxation and cardiac blood supply; it suppresses arteriosclerotic lesions associated with chronic graft rejection; like NO it influences neurotransmission in the hypothalamic-pituitary-adrenal axis and there is evidence that carbon monoxide influences the circadian rhythm of mammals by interacting with NPAS2, the so-called human "clock" protein.

Due to the relevance of carbon monoxide for mammalian physiology, the interest in its medicinal use is growing. Direct carbon monoxide inhalation was tested, but low tolerance to the compound proved contradictory because there is a delicate balance between carbon monoxide-induced tissue hypoxia and therapeutic benefits. Furthermore, the direct gaseous use leads to problems with safety as well as with targeted and controlled delivery. CO-releasing molecules (CO-RMs) represent an alternative approach to the administration of carbon monoxide. A number of complexes have been evaluated and pioneering work of Motterlini and Mann (e.g. Motterlini et al., Circ. Res., 2002 90, E17-24; Motterlini et al., Intensive Care Med. 2008, 34, 649-658; Motterlini et al., Circ. Res. 2002, 90, E17-24; Motterlini et al., Expert. Opin. Investig. Drugs 2005, 14, 1305-1318; Motterlini et al., Curr. Pharm. Des. 2003, 9, 2525-2539; Motterlini et al., J., FASEB J. 2005, 19, 284-286) resulted in the most promising fac-[RuCl(glycinato)(CO)$_3$] complex (CO-RM-3) for controlled carbon monoxide release in vivo. The chemistry and therapeutic effects of CORM-3 are well-documented. CORM-3 releases one mol carbon monoxide within ten minutes after being dissolved in water and significantly reduces blood pressure in vivo and relaxes pre-contracted aortic rings in vitro. Its cardioprotective effects have been documented. Today metal carbonyls have been recognized as a potential new class of pharmaceuticals (for a review on CO-RMs see Johnson et al., Metal Carbonyls in Medicine, Angew. Chem. Int. Ed., 2003, 42, 3722-3729). There are a wide range of documented physiological and medically beneficial effects of CO. It is anti-inflammatory, e.g. it attenuates endotoxic shock and reduces allergic inflammation; it suppresses graft rejection; it protects against hyperoxia and oxidative lung injury; it protects against ischemia and reperfusion injury; it protects pancreatic beta cells from apoptosis; it modulates spermatogenesis under stress conditions; it decreases perfusion pressure; it protects against septic shock and lung injury; it provides cytoprotective effects; it modulates vascular smooth muscle tone, regulates blood pressure under stress conditions and suppresses arteriosclerotic lesions associated with chronic graft rejection and with balloon injury. For CO-RMs aortic vasodilatation, attenuated coronary vasoconstriction and reduction of hypertension was shown. For CO-RM3 inhibition of reperfusion injury, graft rejection and blood platelet aggregation was confirmed.

WO 02/092075 A2 pharmaceutical compositions comprising metal carbonyl compounds teaches, wherein the metal is selected from Fe, Mn, Ru, Rh, Ni, Mo or Co, for stimulating guanylate cyclase activity, neurotransmission or vasodilatation, for treating hypertension, radiation damage, endotoxic shock, inflammation, inflammation-related diseases, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress symptom.

Rhenium is an extremely rare group 7 transition metal that is mainly used for super-alloy and catalyst production. Radioactive isotopes $^{188}$Re and $^{186}$Re are presently used for treatment of liver cancer. They both have similar penetration depths in tissue (5 mm for $^{186}$Re and 11 mm for $^{188}$Re), but $^{186}$Re has the advantage of longer lifetime (90 hours vs. 17 hours for the 188 isotope). Related by periodic trends rhenium has a chemistry similar to technetium. Results on work done to label rhenium onto target compounds can often be transferred to technetium. This transfer aspect has proven useful for radiopharmacy, where it is difficult to work with technetium, especially with the medically used 99m isotope. So far medical applications of rhenium have been limited to the cytotoxic use of its radioactive isotopes.

Very recently Zobi et al. (Inorg. Chem. 2009, 48, 8965-8970) reported the synthesis of carbon monoxide-containing rhenium I and II complexes by means of a versatile synthetic intermediate [Re$^{II}$Br$_4$(CO)$_2$]$^{2-}$, that is stable but sufficiently sensitive to substitution reactions with selected ligands. Due to the unexpected aerobic stability and well-behaved chemistry of complexes derived from this intermediate, the authors very generally speculated on possible medical applications of these Re$^{I/II}$ complexes in medicinal chemistry in the context of conventional Re use, i.e. as cytotoxic isotopes.

It is the object underlying the present invention to provide new medically useful rhenium compounds, preferably medically useful and non-radioactive rhenium compounds. Furthermore, it is an object to provide new carbon monoxide-releasing compounds for medical and/or diagnostic applications, in particular for the prophylaxis and/or treatment of diseases and/or medical conditions selected from the group consisting of cardiovascular diseases, preferably cardiac hypoxia, cardiac infarction, cardiac hypertrophy, arteriosclerosis and hypertension; ischemia-reperfusion injury, inflammatory diseases, preferably asthma or angina; traumatic injury, preferably of the brain, kidney or liver; transplant rejection, preferably allograft and xenograft rejection, platelet aggregation and/or monocyte activation; neuron degeneration of the nervous system, radiation damage, cancer, penile erectile dysfunction, adult respiratory distress syndrome, and disorders of the circadian rhythm of mammals, preferably jet lag.

A further object is to provide (i) new diagnostic and/or medical uses for rhenium compounds, in particular non-radioactive rhenium compounds as well as (ii) pharmaceutical and diagnostic compositions comprising said compounds.

SUMMARY OF THE INVENTION

In a first aspect, the above objects are solved by new compounds of formula (I), preferably for medical use:

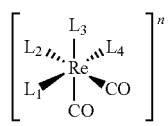

wherein Re is Re(I) or Re(II), preferably Re(II);
n is selected from 3− to 3+, preferably 2−, 1−, 0, 1+ and 2+, more preferably 1−, 0, 1+;
L1, L2, L3 and L4 denote in each case independently of one another pharmaceutically acceptable monodentate ligands.

Preferably, the rhenium metal in the compounds of the present invention is not radioactive.

It was surprisingly found that compounds of formula (I) featuring monodentate ligands to $Re^I$ or $Re^{II}$ do not only demonstrate aerobic stability in solid or dissolved form as previously reported by the inventors (Zobi et al., Inorg. Chem. 2009, 48, 8965-8970), they actually release carbon monoxide under physiological conditions in a controllable manner, the rate of release depending on the nature of the monodentate ligands and the pH.

Compared to the known [RuCl(glycinato)(CO)$_3$] complex designated CO-RM-3 that is presently investigated for therapeutic carbon monoxide release and which has a half-life of about one minute under physiological conditions at pH 7.4 and 37° C., rhenium compounds of the invention have been demonstrated to provide for a carbon monoxide release with a half-life of six minutes to almost an hour. This increased and adjustable delay in the duration and rate of release over CO-RM3 is a significant advantage for the dosing, timing and targeting options of carbon monoxide.

The term "pharmaceutically acceptable" as used herein in the context of the monodentate ligands of the inventive compounds is meant to exclude those ligands that no longer allow for medical utility of the inventive compounds because the adverse effects of the particular ligand, i.e. toxicity, at the dose and the mode administered no longer render the compound medically useful.

Mono- or also called unidentate ligands are those wherein only one atom binds to the central rhenium ion in the compounds of the invention.

For the compounds of the invention Re(II) is preferred because its complexes features 17 electrons, hence, are electronically unsaturated and thus more reactive.

Next to the necessity for pharmaceutically acceptable and monodentate ligands no further structural or functional constraints were identified for the ligands of the compounds of the invention except that they require the presence of either at least one heteroatom, preferably N, O, S and/or P, or at least one carbon-carbon double or triple bond for binding the rhenium metal of the complex. The group of suitable ligands was experimentally verified to encompass water, carbon monoxide, halogens, heteroaromatic and alcoholic compounds, i.e. virtually any compound or atom capable of forming a monodentate rhenium I or II complex together with at least two carbon monoxides.

The ligands can be independently selected from neutral, positively or negatively charged monodentate ligands. In a preferred embodiment the compounds of the invention are those, wherein at least one, preferably two, more preferably three, most preferably all of L1, L2, L3 and L4 are independently selected from the group consisting of neutral or negatively charged, preferably neutral monodentate ligands. Non-limiting examples of suitable positively charged ligands are pyrazinium, pyrimidinium or 4,4'-bipyrimidinium-type ligands, preferably pyrimidinium. Non-limiting examples of suitable neutral ligands are imidazole, pyridine and pyrazine-type ligands, preferably imidazole. Non-limiting examples of suitable negatively charged ligands are cyanide, hydroxide and halogens, preferably hydroxide and halogens, more preferably bromide. Further examples are described throughout the description.

As mentioned before, the monodentate ligands for practicing the invention can be selected from an extremely broad repertoire of chemical compounds of highly diverse nature, e.g. size, charge, spatial and functional arrangement of atoms. Because the present invention is a breakthrough in medicinal rhenium chemistry, vastly expanding the previous very limited use as radioactive cytotoxin and Tc-model compound, there is little information on ligand constraints; and also those highly diverse compounds of the invention already tested do not indicate any constraints. Hence, the ligands for practicing the invention can only be defined functionally without unduly limiting the scope of the invention.

The terms "in each case independently of one another" or "independently selected from the group consisting of" in the context of the monodentate ligands of the inventive rhenium compounds are meant to indicate that the rhenium ligands can be "mixed" ligands, i.e. selected from different members of the group.

The term "independently selected from the group consisting of" is meant to indicate that the four ligands may be selected from the same or different members of the indicated group. It is preferred that at least two ligands are the same; more preferably three ligands are the same and most preferably all four ligands are the same.

In a more preferred embodiment the compounds of the present invention are selected from those, wherein at least one, preferably two, more preferably three, most preferably all of L1, L2, L3 and L4 are independently selected from the group consisting of:
  alkyl and cycloalkyl comprising at least one heteroatom, alkenyl, alkynyl, alkylidene, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxyl, oxo, halogen, trifluoromethyl, nitro, nitrile, isocyanide, alcohol, phosphine, phosphite, phosphonite, sulphide, sulfoxide and amino or guanidine, each amino or guanidine optionally mono-, di- or tri-substituted, preferably mono- or di-substituted by alkyl, acyl or alkoxycarbonyl, each member of the group optionally substituted by one to four R";
wherein each R" is independently selected from
  alkyl, alkenyl, alkynyl, alkylidene, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-, di- or tri-substituted, preferably mono- or di-substituted by alkyl, acyl or alkoxycarbonyl, wherein any members of the group and/or R" are optionally halogenated where possible.

Alkyl ligands comprising at least one heteroatom are preferably $C_{1-20}$, more preferably $C_{1-12}$, most preferably $C_{1-6}$. Cycloalkyl ligands comprising at least one heteroatom are preferably $C_{3-20}$, more preferably $C_{3-12}$, more preferably $C_{3-6}$ and most preferably $C_{5-6}$. Alkenyl, alkynyl and alkylidene ligands are preferably $C_{2-20}$, more preferably $C_{2-12}$, most preferably $C_{2-6}$. Aryl, heteroaryl, arylalkyl and aryloxy ligands are preferably $C_{5-20}$, more preferably $C_{5-12}$, most preferably $C_{5-6}$. Alkoxy, alkylthio, acyl, alkoxycarbonyl, acyloxy, acylamino and alkylsulfonyl are preferably $C_{1-20}$, more preferably $C_{1-12}$, most preferably $C_{1-6}$.

With respect to the stereochemistry of the compounds of the invention, it is preferred that the at least two carbon monoxides have a cis configuration towards each other, i.e. a cis-$[Re^{I/II}(CO)_2L_{1-4}]$ stereochemistry. In a more preferred embodiment, at least two of the four ligands $L_{1-4}$ are of the same type, preferably are halogens, more preferably bromide and have a trans configuration. This leaves a cis configuration for the remaining two ligands resulting in a cis-trans-cis stereochemistry, i.e. cis-trans-cis-$[Re^{I/II}(CO)_2(L_1L_4)(L_2L_3)]$, wherein L1 and L4 are preferably halogens, more preferably Br. Hence, in a most preferred embodiment, the invention is directed to cis-trans-cis $[Re^{I/II}(CO)_2(halogen)_2(L2L3)]$ compounds, bromides being the preferred halogens.

Preferred compounds of the invention are those, wherein the at least two carbon monoxide ligands are in a cis configuration towards each other and/or at least two of L1, L2, L3 and L4 are halogen, preferably bromide and/or the at least two halogen are in a trans configuration towards each other.

In a further preferred embodiment the compounds of the present invention are selected from those, wherein at least one, preferably two, more preferably three, most preferably four of L1, L2, L3 and L4 are independently selected from the group consisting of $C_{1-12}$ alkyl and $C_{3-12}$ cycloalkyl comprising at least one heteroatom, preferably $C_{1-6}$ alkyl and $C_{3-7}$ cycloalkyl, $C_{2-12}$ alkenyl, preferably $C_{2-6}$ alkenyl, $C_{2-12}$ alkynyl, preferably $C_{2-6}$ alkynyl, $C_{2-12}$ alkylidene, preferably $C_{2-6}$ alkylidene, $C_{1-12}$ alkoxy, preferably $C_{1-6}$ alkoxy, $C_{1-12}$ alkylthio, preferably $C_{1-6}$ alkylthio, $C_{1-12}$ acyl, preferably $C_{1-6}$ acyl, $C_{2-12}$ alkoxycarbonyl, preferably $C_{2-7}$ alkoxycarbonyl, $C_{1-12}$ acyloxy, preferably $C_{1-6}$ acyloxy, $C_{1-12}$ acylamino, preferably $C_{1-6}$ acylamino, indanyl, indenyl, phenyl naphthyl, heteroaryl selected from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl and heterocyclyl selected from aziridinyl, pyrrolidinyl, pyrrolinyl, morpholinyl, thiomorpholinyl, tetrahydrofuranyl, dioxalanyl, pyranyl, piperidinyl and piperazinyl, each optionally substituted by one to four R";

wherein each R" is independently selected from $C_{1-5}$ alkyl, $C_{2-5}$ alkenyl, $C_{2-5}$ alkynyl, $C_{2-5}$ alkylidene, $C_{3-7}$ cycloalkyl, aryl, arylalkyl, aryloxy, $C_{1-5}$ alkoxy, $C_{1-3}$ alkylthio, $C_{1-3}$ acyl, $C_{2-7}$ alkoxycarbonyl, $C_{1-5}$ acyloxy, $C_{1-5}$ acylamino, sulphonylamino, aminosulfonyl, alkylsulfonyl, carboxy, carboxamide, hydroxy, halogen, trifluoromethyl, nitro, nitrile and amino optionally mono-, di- or tri-substituted, preferably mono- or di-substituted by $C_{1-6}$ alkyl, $C_{1-6}$ acyl or $C_{2-7}$ alkoxycarbonyl, wherein any members of the group and/or R" are optionally halogenated where possible.

In a further preferred embodiment the compounds of the present invention are selected from those, wherein at least one, preferably two, more preferably three, most preferably four of L1, L2, L3 and L4 are independently selected from the group consisting of (i) halides, preferably Br⁻, OH⁻, CN⁻, ClO₄⁻, NO₃⁻, NO₂⁻, NCO⁻, NCS⁻, N3⁻ and

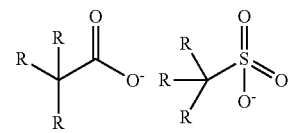

(ii) water, carbon monoxide and nitrogen, and
(iii) nitriles, isocyanides, primary, secondary and tertiary amines, preferably primary and secondary amines, alcohols, phosphines, phosphates, phosphonites, sulfides, sulfoxides, each optionally substituted by one to four R" where possible;

wherein each R and/or R" is independently selected from alkyl, alkenyl, alkynyl, alkylidene, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-, di- or tri-substituted by alkyl, acyl or alkoxycarbonyl, wherein any of the groups and/or R" are optionally halogenated where possible;

preferably, wherein each R and/or R" is independently selected from $C_{1-6}$ alkyl, $C_{2-6}$ alkenyl, $C_{2-6}$ alkynyl, $C_{2-6}$ alkylidene, $C_{3-7}$ cycloalkyl, aryl, arylalkyl, aryloxy, $C_{1-5}$ alkoxy, $C_{1-6}$ alkylthio, $C_{1-6}$ acyl, $C_{2-7}$ alkoxycarbonyl, $C_{1-6}$ acyloxy, $C_{1-6}$ acylamino, sulphonylamino, aminosulfonyl, $C_{1-6}$ alkylsulfonyl, carboxy, carboxamide, hydroxy, halogen, trifluoromethyl, nitro, nitrile and amino optionally mono-, di- or tri-substituted, preferably mono- or di-substituted by $C_{1-6}$ alkyl, $C_{1-6}$ acyl or $C_{2-7}$ alkoxycarbonyl, wherein any of the groups and/or R" are optionally halogenated where possible.

In a further preferred embodiment the compounds of the present invention are selected from those, wherein at least one, preferably two, more preferably three, most preferably four of L1, L2, L3 and L4 are independently selected from the group of 5- or 6-membered heteroatomic (the heteroatoms is/are preferably at least one of N, O, S and/or P) carbon rings, preferably consisting of

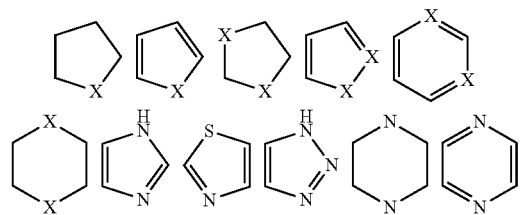

wherein X is selected from N, O, S or P with the proviso that for ligands with two X, one X may be C, optionally substituted by one to four R" where possible;

wherein each R" is independently selected from
   alkyl, alkenyl, alkynyl, alkylidene, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-, di- or tri-substituted, preferably mono- or di-substituted by alkyl, acyl or alkoxycarbonyl, wherein any of the groups and/or R" are optionally halogenated where possible;

or preferably, wherein each R" is independently selected from
   $C_{1-6}$ alkyl, $C_{2-6}$ alkenyl, $C_{2-6}$ alkynyl, $C_{2-6}$ alkylidene, $C_{3-7}$ cycloalkyl, aryl, arylalkyl, aryloxy, $C_{1-6}$ alkoxy, $C_{1-6}$ alkylthio, $C_{1-6}$ acyl, $C_{2-7}$ alkoxycarbonyl, $C_{1-6}$ acyloxy, $C_{1-6}$ acylamino, sulphonylamino, aminosulfonyl, $C_{1-6}$ alkylsulfonyl, carboxy, carboxamide, hydroxy, halogen, trifluoromethyl, nitro, nitrile and amino optionally mono-, di- or tri-substituted, preferably mono- or di-substituted by $C_{1-6}$ alkyl, $C_{1-6}$ acyl or $C_{2-7}$ alkoxycarbonyl, wherein any member of the group and/or R" are optionally halogenated where possible.

In a further preferred embodiment the compounds of the present invention are selected from those, wherein at least one, preferably two, more preferably three, most preferably four of L1, L2, L3 and L4 are independently selected from the group consisting of 5 to 6-membered heteroatomic (preferably N, O, S and/or P) carbon rings, preferably those described directly above, wherein 2 to 8, preferably 2 to 6, more preferably 2 to 4 of the 5 to 6-membered heteroatomic carbon rings are bound to a common linker, e.g.

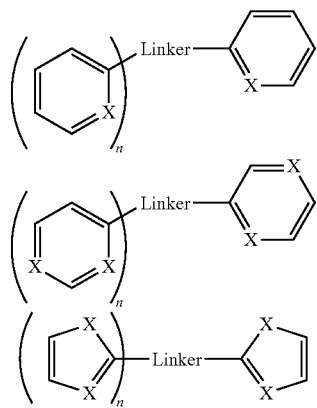

wherein X is defined as above and n is preferably 1 to 7, more preferably 1 to 5; and "linker" denotes a functional group connecting the at least two 5 to 6-membered
   heteroatomic carbon rings in the ligand, preferably a linker selected from the group consisting of alkyl, alkenyl, alkynyl, alkylidene, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl;
   more preferably a linker selected from the group consisting of $C_{1-12}$, preferably $C_{1-6}$ alkyl, $C_{1-12}$, preferably $C_{1-6}$ alkenyl, $C_{1-12}$, preferably $C_{1-6}$ alkynyl, $C_{1-12}$, preferably $C_{1-6}$ alkylidene, $C_{1-12}$, preferably $C_{1-6}$ cycloalkyl, aryl, heteroaryl, arylalkyl, aryloxy, $C_{1-12}$, preferably $C_{1-6}$ alkoxy, $C_{1-12}$, preferably $C_{1-6}$ alkylthio, $C_{1-12}$, preferably $C_{1-6}$ acyl, $C_{1-12}$, preferably $C_{1-6}$ alkoxycarbonyl, $C_{1-12}$, preferably $C_{1-6}$ acyloxy, $C_{1-12}$, preferably $C_{1-6}$ acylamino, sulphonylamino, aminosulfonyl, $C_{1-12}$, preferably $C_{1-6}$ alkylsulfonyl;

each compound optionally substituted by one to four R" where possible;

wherein each R" is independently selected from the group consisting of
   alkyl, alkenyl, alkynyl, alkylidene, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-, di- or tri-substituted, preferably mono- or disubstituted by $C_{1-6}$ alkyl, $C_{1-6}$ acyl or $C_{2-7}$ alkoxycarbonyl;

preferably each R" is independently selected from the group consisting of $C_{1-12}$ alkyl, $C_{2-12}$ alkenyl, $C_{2-12}$ alkynyl, $C_{2-12}$ alkylidene, $C_{3-12}$ cycloalkyl, aryl, arylalkyl, aryloxy, $C_{1-12}$ alkoxy, $C_{1-12}$ alkylthio, $C_{1-12}$ acyl, $C_{2-12}$ alkoxycarbonyl, $C_{1-12}$ acyloxy, $C_{1-12}$ acylamino, sulphonylamino, aminosulfonyl, $C_{1-12}$ alkylsulfonyl, carboxy, carboxamide, hydroxy, halogen, trifluoromethyl, nitro, nitrile and amino optionally mono-, di- or tri-substituted, preferably mono- or disubstituted by $C_{1-6}$ alkyl, $C_{1-6}$ acyl or $C_{2-7}$ alkoxycarbonyl;

more preferably, wherein each R" is independently selected from the group consisting of $C_{1-6}$ alkyl, $C_{2-6}$ alkenyl, $C_{2-6}$ alkynyl, $C_{2-6}$ alkynyl, $C_{2-6}$ alkylidene, $C_{3-7}$ cycloalkyl, aryl, arylalkyl, aryloxy, $C_{1-6}$ alkoxy, $C_{1-6}$ alkylthio, $C_{1-6}$ acyl, $C_{2-7}$ alkoxycarbonyl, $C_{1-6}$ acyloxy, $C_{1-6}$ acylamino, sulphonylamino, aminosulfonyl, alkylsulfonyl, carboxy, carboxamide, hydroxy, halogen, trifluoromethyl, nitro, nitrile and amino optionally mono-, di- or tri-substituted by $C_{1-6}$ alkyl, $C_{1-6}$ acyl or $C_{2-7}$ alkoxycarbonyl, wherein any of the linkers and/or R" are optionally halogenated where possible;

wherein the rhenium-coordinating atom preferably forms part of an aromatic system.

In a further preferred embodiment the compounds of the present invention are selected from those, wherein at least one, preferably two, more preferably three, most preferably four of L1, L2, L3 and L4 are independently selected from the group consisting of

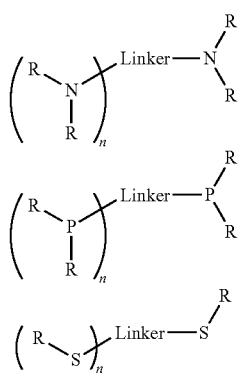

wherein n is 1 to 6, preferably 1 to 3;
"linker" denotes a functional group connecting the two nitrogen, two phosphor or two sulphur atoms,
   preferably a linker selected from the group consisting of alkyl, alkenyl, alkynyl, alkylidene, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl;

more preferably a linker selected from the group consisting of $C_{1-12}$, preferably $C_{1-6}$ alkyl, $C_{1-12}$, preferably $C_{1-6}$ alkenyl, $C_{1-12}$, preferably $C_{1-6}$ alkynyl, $C_{1-12}$, preferably $C_{1-6}$ alkylidene, $C_{1-12}$, preferably $C_{1-6}$ cycloalkyl, aryl, heteroaryl, arylalkyl, aryloxy, $C_{1-12}$, preferably $C_{1-6}$ alkoxy, $C_{1-12}$, preferably $C_{1-6}$ alkylthio, $C_{1-12}$, preferably $C_{1-6}$ acyl, $C_{1-12}$, preferably $C_{1-6}$ alkoxycarbonyl, $C_{1-12}$, preferably $C_{1-6}$ acyloxy, $C_{1-12}$, preferably $C_{1-6}$ acylamino, sulphonylamino, aminosulfonyl, $C_{1-12}$, preferably $C_{1-6}$ alkylsulfonyl;

wherein each R is independently selected from the group consisting of alkyl, alkenyl, alkynyl, alkylidene, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-, di- or tri-substituted, preferably mono- or disubstituted by $C_{1-6}$ alkyl, $C_{1-6}$ acyl or $C_{2-7}$ alkoxycarbonyl;

preferably wherein each R is independently selected from the group consisting of $C_{1-12}$ alkyl, $C_{2-12}$ alkenyl, $C_{2-12}$ alkynyl, $C_{2-12}$ alkylidene, $C_{3-12}$ cycloalkyl, aryl, arylalkyl, aryloxy, $C_{1-12}$ alkoxy, $C_{1-12}$ alkylthio, $C_{1-12}$ acyl, $C_{2-12}$ alkoxycarbonyl, $C_{1-12}$ acyloxy, $C_{1-12}$ acylamino, sulphonylamino, aminosulfonyl, $C_{1-12}$ alkylsulfonyl, carboxy, carboxamide, hydroxy, halogen, trifluoromethyl, nitro, nitrile and amino optionally mono-, di- or tri-substituted, preferably mono- or disubstituted by $C_{1-6}$ alkyl, $C_{1-6}$ acyl or $C_{2-7}$ alkoxycarbonyl;

more preferably, wherein each R is independently selected from the group consisting of $C_{1-6}$ alkyl, $C_{2-6}$ alkenyl, $C_{2-6}$ alkynyl, $C_{2-6}$ alkynyl, $C_{2-6}$ alkylidene, $C_{3-7}$ cycloalkyl, aryl, arylalkyl, aryloxy, $C_{1-6}$ alkoxy, $C_{1-6}$ alkylthio, $C_{1-6}$ acyl, $C_{2-7}$ alkoxycarbonyl, $C_{1-6}$ acyloxy, $C_{1-6}$ acylamino, sulphonylamino, aminosulfonyl, $C_{1-6}$ alkylsulfonyl, carboxy, carboxamide, hydroxy, halogen, trifluoromethyl, nitro, nitrile and amino optionally mono-, di- or tri-substituted by $C_{1-5}$ alkyl, $C_{1-6}$ acyl or $C_{2-7}$ alkoxycarbonyl, wherein any of the R are optionally halogenated where possible.

In a further preferred embodiment the compounds of the present invention are selected from those, wherein at least one, preferably at least two, more preferably at least three and most preferably four of L1, L2, L3 and L4 are independently selected from the group consisting of nucleotides, amino acids, vitamins, preferably vitamin B12, and oligomers of 1 to 10 moieties thereof, preferably

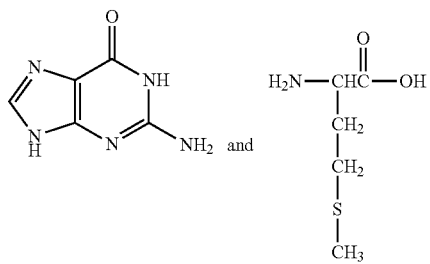

optionally substituted by one to four R" where possible; wherein each R" is independently selected from alkyl, alkenyl, alkynyl, alkylidene, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-, di- or tri-substituted, preferably mono- or disubstituted by $C_{1-6}$ alkyl, $C_{1-6}$ acyl or $C_{2-7}$ alkoxycarbonyl;

preferably wherein each R" is independently selected from $C_{1-12}$ alkyl, $C_{2-12}$ alkenyl, $C_{2-12}$ alkynyl, $C_{2-12}$ alkylidene, $C_{3-12}$ cycloalkyl, aryl, arylalkyl, aryloxy, $C_{1-12}$ alkoxy, $C_{1-12}$ alkylthio, $C_{1-12}$ acyl, $C_{2-12}$ alkoxycarbonyl, $C_{1-12}$ acyloxy, $C_{1-12}$ acylamino, sulphonylamino, aminosulfonyl, $C_{1-12}$ alkylsulfonyl, carboxy, carboxamide, hydroxy, halogen, trifluoromethyl, nitro, nitrile and amino optionally mono-, di- or tri-substituted, preferably mono- or disubstituted by $C_{1-6}$ alkyl, $C_{1-6}$ acyl or $C_{2-7}$ alkoxycarbonyl;

more preferably, wherein each R" is independently selected from $C_{1-6}$ alkyl, $C_{2-6}$ alkenyl, $C_{2-6}$ alkynyl, $C_{2-6}$ alkynyl, $C_{2-6}$ alkylidene, $C_{3-7}$ cycloalkyl, aryl, arylalkyl, aryloxy, $C_{1-6}$ alkoxy, $C_{1-6}$ alkylthio, $C_{1-6}$ acyl, $C_{2-7}$ alkoxycarbonyl, $C_{1-6}$ acyloxy, $C_{1-6}$ acylamino, sulphonylamino, aminosulfonyl, $C_{1-6}$ alkylsulfonyl, carboxy, carboxamide, hydroxy, halogen, trifluoromethyl, nitro, nitrile and amino optionally mono-, di- or tri-substituted by $C_{1-5}$ alkyl, $C_{1-5}$ acyl or $C_{2-7}$ alkoxycarbonyl, wherein any of the R" are optionally halogenated where possible.

In a most preferred embodiment the compounds of the present invention have formula $[Re^{II}Br_2(CO)_2(L)_2]$, preferably cis-trans-cis $[Re^{II}Br_2(CO)_2(L)_2]$, wherein at least one, preferably both L are selected from the group consisting of halides, preferably $Br^-$, carbon monoxide, N-methyl imidazole, benzimidazole, 4-methylpyridine, imidazole, pyridine, pyridine, $C_{1-6}$ alkyl cyanide, preferably methyl cyanide and alcohol, preferably $C_{1-6}$ alcohol, more preferably methanol or ethanol, optionally substituted by one to four R" where possible;

wherein each R" is independently selected from the group consisting of alkyl, alkenyl, alkynyl, alkylidene, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-, di- or tri-substituted, preferably mono- or disubstituted by $C_{1-6}$ alkyl, $C_{1-6}$ acyl or $C_{2-7}$ alkoxycarbonyl;

preferably wherein each R" is independently selected from the group consisting of $C_{1-12}$ alkyl, $C_{2-12}$ alkenyl, $C_{2-12}$ alkynyl, $C_{2-12}$ alkylidene, $C_{3-12}$ cycloalkyl, aryl, arylalkyl, aryloxy, $C_{1-12}$ alkoxy, $C_{1-12}$ alkylthio, $C_{1-12}$ acyl, $C_{2-12}$ alkoxycarbonyl, $C_{1-12}$ acyloxy, $C_{1-12}$ acylamino, sulphonylamino, aminosulfonyl, $C_{1-12}$ alkylsulfonyl, carboxy, carboxamide, hydroxy, halogen, trifluoromethyl, nitro, nitrile and amino optionally mono-, di- or tri-substituted, preferably mono- or disubstituted by $C_{1-6}$ alkyl, $C_{1-6}$ acyl or $C_{2-7}$ alkoxycarbonyl;

more preferably, wherein each R" is independently selected from the group consisting of $C_{1-6}$ alkyl, $C_{2-6}$ alkenyl, $C_{2-6}$ alkynyl, $C_{2-6}$ alkynyl, $C_{2-6}$ alkylidene, $C_{3-7}$ cycloalkyl, aryl, arylalkyl, aryloxy, $C_{1-6}$ alkoxy, $C_{1-6}$ alkylthio, $C_1$ acyl, $C_{2-7}$ alkoxycarbonyl, $C_{1-6}$ acyloxy, $C_{1-6}$ acylamino, sulphonylamino, aminosulfonyl, $C_{1-6}$ alkylsulfonyl, carboxy, carboxamide, hydroxy, halogen, trifluoromethyl, nitro, nitrile and amino optionally mono-, di- or tri-substituted by $C_{1-6}$ alkyl, $C_{1-6}$ acyl or $C_{2-7}$ alkoxycarbonyl, wherein any members of the group and/or of the R" are optionally halogenated where possible.

Because the monodentate ligands for practicing the invention can be selected from an extremely broad repertoire of chemical compounds of highly diverse nature, e.g. size, charge, spatial and functional arrangement of atoms, the compounds of the invention may comprise at least one, preferably two diagnostic and/or physiologically active ligands, preferably selected from the group consisting of targeting ligands, diagnostic ligands and physiologically, preferably medically active ligands. Hence, the compounds of the invention can function as a "carrier" for "functional" ligands.

The invention includes the use of any compounds described above containing one or more asymmetric carbon atoms which may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations. Some of the compounds of the invention can exist in more than one tautomeric form. The invention includes all such tautomers.

For all compounds disclosed herein, in the event that the nomenclature conflicts with the structure, it shall be understood that the compound is defined by the structure.

All terms as used in this specification, unless otherwise stated, shall be understood by their ordinary meaning in the art.

The term "heteroatom", as used herein, for example in the context of the term heteroaryl shall be understood to mean atoms other than carbon and hydrogen such as and preferably O, N, S and P.

The terms alkyl, alkenyl, alkynyl, alkylidene, etc. shall be understood as encompassing linear and branched, substituted or non-substituted forms of carbon-containing chains where structurally possible. In these carbon chains one or more carbon atoms can be optionally replaced by heteroatoms, preferably by O, S or N. If N is not substituted, it is NH. The heteroatoms may replace either terminal or internal carbon atoms within a linear or branched carbon chain. Such groups can be substituted as herein described by groups such as oxo to result in definitions such as but not limited to alkoxycarbonyl, acryl, amido and thioxo.

The term "carbocycle" shall be understood to mean a cyclic hydrocarbon containing from 3 to 20, preferably 3 to 12 carbon atoms, more preferably 5 or 6 carbon atoms. Carbocycles include hydrocarbon rings containing from 3 to 20, preferably 3 to 12 carbon atoms. These carbocycles may be either aromatic or non-aromatic, i.e. cycloalkyl systems or mixed cycloalkyl-aromatic systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl, and benzocycloheptenyl. Certain terms for cycloalkyl such as cyclobutanyl and cyclobutyl shall be used interchangeably.

The term "cycloalkyl" shall be understood to mean aliphatic hydrocarbon-containing rings having from 3 to 20, preferably 3 to 12 carbon atoms. These non-aromatic ring systems may be mono- or polyunsaturated, i.e. the term encompasses cycloalkenyl and cycloalkynyl. The cycloalkyl may comprise heteroatoms, preferably O, S or N, and be substituted or non-substituted. Preferred and non-limiting cycloalkyls include cyclopropyl, cyclobutyl, cyclopentyl, cyclopentenyl, cyclohexyl, cyclohexenyl, cycloheptanyl, cycloheptenyl, benzocyclobutanyl, benzocycloheptanyl and benzocycloheptenyl.

The term "heterocyclic" refers to a stable non-aromatic, preferably 3 to 20-membered, more preferably 3 to 12-membered, most preferably 5 or 6-membered, monocyclic or multicyclic, preferably 8 to 12-membered bicyclic, heteroatom-containing cyclic compound, that may be either saturated or unsaturated. Each heterocycle consists of carbon atoms and one or more, preferably 1 to 4 heteroatoms chosen from nitrogen, oxygen, sulphur and phosphorus. The heterocyclic residue may be bound to the remaining structure of the complete molecule by any atom of the cycle, which results in a stable structure. Exemplary heterocycles include, but are not limited to, pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λ4-thiomorpholinyl, 13-oxa-11-aza-tricyclo [7.3.1.0-2,7]tridecy-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulphide, pentamethylene sulfoxide, pentamethylene sulfone, tetramethylene sulphide, tetramethylene sulfoxide and tetramethylene sulfone.

The term "aryl" as used herein shall be understood to mean an aromatic carbocycle or heteroaryl as defined herein. Each aryl or heteroaryl unless otherwise specified includes its partially or fully hydrogenated derivatives. For example, quinolinyl may include decahydroquinolinyl and tetrahydroquinolinyl; naphthyl may include its hydrogenated derivatives such as tetrahydronaphthyl. Other partially or fully hydrogenated derivatives of the aryl and heteroaryl compounds described herein will be apparent to one of ordinary skill in the art. Naturally, the term encompasses aralkyl and alkylaryl, both of which are preferred embodiments for practicing the compounds of the present invention. For example, the term aryl encompasses phenyl, indanyl, indenyl, dihydronaphthyl, tetrahydronaphthyl, naphthyl and decahydronaphthyl.

The term "heteroaryl" shall be understood to mean an aromatic $C_3$-$C_{20}$, preferably 5 to 8-membered monocyclic or preferably 8 to 12-membered bicyclic ring containing 1 to 4 heteroatoms such as N, O, P and S. Exemplary heteroaryls comprise aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazole[3,4-b] pyridinyl, tubercidinyl, oxazo[4,5-b]pyridinyl and imidazo [4,5-b]pyridinyl.

Terms which are analogues of the above cyclic moieties such as aryloxy or heteroaryl amine shall be understood to mean an aryl, heteroaryl, heterocycle as defined above attached to its respective group.

As used herein, the terms "nitrogen", "sulphur" and phosphorus include any oxidized form of nitrogen, sulphur and phosphorus and the quaternized form of any basic nitrogen as long as the resulting compound is chemically stable. For example, an —S—$C_{1-6}$ alkyl radical shall be understood to include —S(O)—$C_{1-6}$ alkyl and —S(O)$_2$—$C_{1-6}$ alkyl.

The compounds of the invention are only those which are contemplated to be 'chemically stable' as will be appreciated by those skilled in the art. For example, compounds having a 'dangling valency' or a 'carbanion' are not compounds contemplated by the inventive concept disclosed herein.

Pharmaceutically acceptable salts of the compounds of the invention include those derived from pharmaceutically acceptable inorganic and organic acids and bases, preferably non-oxidizing inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, ethanesulfonic, formic, benzoic, malonic, naphthalene-2-sulfuric and benzenesulfonic acids. Salts derived from appropriate bases include alkali metal (e.g., sodium), alkaline earth metal (e.g., magnesium), ammonium and N—$(C_{1-4}$ alkyl$)_4^+$ salts.

In another aspect, the present invention relates to a pharmaceutical composition comprising a pharmaceutically effective amount of at least one compound according to the invention as described above and optionally one or more pharmaceutically acceptable carriers and/or adjuvants.

The pharmaceutical compositions of the present invention typically comprise a pharmaceutically acceptable excipient, carrier, buffer, stabiliser, preservative and/or other materials well known to those skilled in the art. Such materials should be non-toxic and should not interfere unduly with the efficacy of the active ingredient. The precise nature of the carrier or other material may depend on the route of administration, e.g. oral, intravenous, subcutaneous, nasal, intramuscular, intraperitoneal or suppository routes. Pharmaceutical compositions for oral administration may be in tablet, capsule, powder or liquid form. A tablet may include a solid carrier such as gelatin or an adjuvant or a slow-release polymer. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Pharmaceutically acceptable amounts of other solvents may also be included, in particular where they are required for dissolving the particular metal carbonyl compound contained in the composition. For intravenous, cutaneous or subcutaneous injection or injection at the site of affliction the active ingredient will typically be in the form of a parenterally acceptable solution which is pyrogen-free and has suitable pH, isotonicity and stability. Those of skill in the pharmaceutical art are capable of preparing suitable solutions using, for example, isotonic vehicles such as physiological saline, Ringer's injection solution and Ringer's lactate solution for injection. Preservatives, stabilisers, buffers, antioxidants and/or other additives may be included, as required. Delivery systems for needle-free injection are also known, and compositions of the invention for use with such systems may be prepared accordingly.

In a further aspect, the present invention relates to a use of a compound of the invention as defined above for the preparation of a medicament for the treatment and/or protection of patients having or being prone to produce a disease or medical condition responsive to carbon monoxide treatment, preferably a disease or medical condition involving hypoxic, anoxic and/or inflamed mammalian tissue, preferably a tissue selected from the group consisting of heart, lung, liver, brain, gut, kidney, muscle, bone, skin and eye, preferably a disease or medical condition selected from the group consisting of cardiovascular diseases, preferably cardiac hypoxia, cardiac infarction, cardiac hypertrophy, arteriosclerosis and hypertension; ischemia-reperfusion injury, inflammatory diseases, preferably asthma or angina; traumatic injury, preferably of the brain, kidney or liver; transplant rejection, preferably allograft and xenograft rejection, platelet aggregation and/or monocyte activation; neuron degeneration of the nervous system, radiation damage, cancer, penile erectile dysfunction, adult respiratory distress syndrome, and disorders of the circadian rhythm of mammals, preferably jet lag.

The above diseases or medical conditions have been established as being responsive to carbon monoxide administration (see WO 02/092075 and Johnson et al., Metal carbonyls in Medicine, Angew. Chem. Int. Ed. 2003, 42, 3722-3729.)

The pharmaceutical composition/medicament is for administration prior to, after or concomitantly to a medical condition.

As used herein, a "patient" means any mammal that may benefit from a treatment with the compounds of the invention. Preferably, a "patient" is selected from the group consisting of laboratory animals (e.g. mouse or rat), domestic animals (including e.g. guinea pig, rabbit, pig, sheep, goat, camel, cow, horse, donkey, cat, or dog), or primates including human beings. It is particularly preferred that the "patient" is a human being.

As used herein, "treat", "treating" or "treatment" of a disease, medical condition or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "administering" includes in vivo administration, as well as administration directly to tissue ex vivo, such as vein grafts. Administration may be effected for the prevention, i.e. before clinical occurrence of a disease or disorder, or for treatment, i.e. after clinical occurrence of a disease or disorder.

In a preferred embodiment, the present invention is directed to the use of the above-mentioned compounds for preparing a medicament for the treatment of a disease or medical condition selected from the group consisting of selected from the group consisting of cardiovascular diseases, preferably cardiac hypoxia, cardiac infarction, cardiac hypertrophy, arteriosclerosis and hypertension; ischemia-reperfusion injury, inflammatory diseases, preferably asthma or angina; traumatic injury, preferably of the brain, kidney or liver; transplant rejection, preferably allograft and xenograft rejection, platelet aggregation and/or monocyte activation; neuron degeneration of the nervous system, radiation damage, cancer, penile erectile dysfunction, adult respiratory distress syndrome, and disorders of the circadian rhythm of mammals, preferably jet lag.

Methods of Use

In a further aspect, the present invention relates to a method of treating and/or protecting patients having or being prone to develop a disease or medical condition responsive to carbon monoxide treatment as discussed above, the method comprising the administration of a therapeutically effective amount of at least one compound of the invention as defined above or a prodrug thereof or an effective amount of the pharmaceutical composition of the invention as defined above to a patient in need thereof.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

For therapeutic or prophylactic use the compounds of the invention may be administered in any conventional dosage form in any conventional manner. Routes of administration include, but are not limited to, intravenously, intramuscularly, cutaneously, subcutaneously, intrasynovially, by infusion, sublingually, transdermally, orally, or topically. The preferred modes of administration is intravenous.

The compounds may be administered alone or in combination with adjuvants that enhance stability of the compounds, facilitate administration of pharmaceutical compositions containing them in certain embodiments, provide increased dissolution or dispersion, provide adjunct therapy, and the like, including other active ingredients. Advantageously such combination therapies utilize lower dosages of the conventional therapeutics, thus avoiding possible toxicity and adverse side-effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US01/21860 and U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regimen.

As mentioned above, dosage forms of the compounds described herein include pharmaceutically acceptable carriers and adjuvants known to those of ordinary skill in the art. These carriers and adjuvants include, for example, ion exchangers, alumina, aluminium stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Controlled release dosage forms with or without immediate release portions are also envisaged. Methods for preparing such dosage forms are known (see, for example, H. C. Ansel and N. G. Popovish, *Pharmaceutical Dosage Forms and Drug Delivery Systems*, 5$^{th}$ ed., Lea and Febiger (1990)). Dosage levels and requirements are well-recognized in the art and may be selected by those of ordinary skill in the art from available methods and techniques suitable for a particular patient. In some embodiments, dosage levels range from about 0.1-100 g/dose for a 70 kg patient. Although one dose per day may be sufficient, up to 5 doses per day may be given. For oral doses, up to 2000 mg/day or more may be required.

Reference in this regard may also be made to U.S. provisional application no. 60/339,249. As the skilled artisan will appreciate, lower or higher doses may be required depending on particular factors. For instance, specific doses and treatment regimens will depend on factors such as the patient's general health profile, the severity and course of the patient's disorder or disposition thereto, and the judgment of the treating physician.

For further information on how to formulate and administer the carbon monoxide releasing rhenium compounds of the invention, reference is made to the following documents WO 2005/013691 A1, WO 2009/013612, US 2007/0207993, US 2007/0207217, US 2006/0233890, US 2006/0148900 and US 2004/0067261.

In another aspect, the present invention relates to compounds of formula (I) as described above, preferably non-radioactive compounds, more preferably with the proviso that the compound is not selected from the group explicitly disclosed in the recent publication of the present inventors (Zobi et al., Inorg. Chem. 2009, 48, 8965-8970), the group preferably consisting of $[Re^{II}Br_4(CO)_2]^{2-}$, $[Re^{II}Br_2(CO)_2(pyridine)_2]$, $[Re^{II}Br_2(CO)_2(imidazole)_2]$, $[Re^{II}(CO)_2(HOCH_3)_4]^{2+}$, $[Re^{II}Br_3(CO)_2(N\equiv CCH_3)]^-$, $[Re^{II}Br_3(CO)_3]^{2-}$, $[Re^{I}Br_2(CO)_2(imidazole)_2]^-$, $[Re^{I}Br_2(CO)_2(N\equiv CCH_3)_2]$ and $[Re^{I}(CO)_3(H_2O)_3]^+$.

The following tables, figures and examples are merely illustrative of the present invention and should not be construed to limit the scope of the invention as indicated by the appended claims in any way.

EXAMPLES

Example 1

Methods of Preparation

Figure 1:
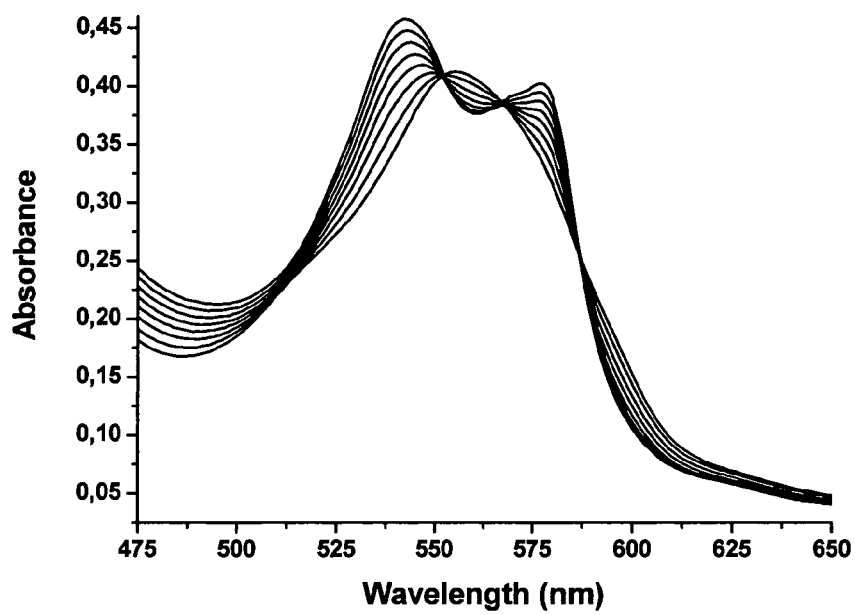
FIG. 1 graphically represents a typical absorption spectrum of the conversion of deoxy-myoglobin (Mb) to carbon monoxide myoglobin (MbCO) by a cis-trans-[$Re^{II}(CO)_2Br_2L2$]n complex exemplified with a 30 μM Mb solution after the addition of compound 4 (30 μM, 25° C., 0.1 M phosphate buffer, pH 7.4).

The compounds of the present invention can be prepared without any undue burden or inventive skill by any appropriate conventional synthetic strategy known to those of skill in organic and inorganic chemistry, in particular in view of the recent disclosure of the present inventors in Inorg. Chem. 2009, 48, 8965-8970, the synthetic routes of which are incorporated in toto by reference herewith.

Chemicals and solvents were purchased from standard sources, distilled and/or degassed where necessary prior to use. $(NEt_4)_2[ReBr_3(CO)_3]$, compounds 1, 2, 6, 7, 12 and 13 were synthesized as previously described (Zobi et al., Inorg. Chem. 2009, 48, 8965-8970; Alberto et al. J. Chem. Soc. Dalton Trans. 1994, 2815-2820; Abram et al., Z. Anorg. Allg. Chem. 1996, 622, 813-818). All other complexes were synthesized under nitrogen with standard techniques. Elemental analyses (EA) were performed on a Leco CHNS-932 elemental analyser. IR spectra were recorded in a PerkinElmer Spectrum BX FT-IR spectrometer. Crystallographic data were collected at 183(2) K with Mo $K_\alpha$ radiation ($\lambda$=0.7107 Å) that was monochromated with help of a graphite on an Oxford Diffraction Xcalibur system with a Ruby detector. Suitable crystals were covered with oil (Infineum V8512), mounted on top of a glass fiber and immediately transferred to the diffractometer. The program suite CrysAlis$^{Pro}$ was used for data collection, semi-empirical absorption correction and data reduction. Structures were solved with direct methods using SIR97 and were refined by full-matrix least-squares methods on $F^2$ with SHELXL-97. The structures were checked for higher symmetry using the program Platon.

Example 2

Detection of CO Release Using the Myoglobin Assay

The release of CO from the compounds of the invention was assessed spectrophotometrically by measuring the conversion of deoxymyoglobin (Mb) to carbonmonoxy myoglobin (MbCO) as previously reported (Clark et al., Circ. Res. 2003, 93, e2-8; Motterlini et al., Circ. Res. 2002, 90, E17-24; Motterlini et al., Curr. Pharm. Des. 2003, 9, 2525-2539). A small aliquot of a freshly prepared concentrated solution of the selected Re complex (compound 2 in methanol, in DMSO for all other complexes) was added to 1 ml of the Mb solution in phosphate buffer prepared at different pHs (7.4, 6.3 and 5.8; final concentrations: 30 µM for Re complex and Mb). Changes in the Mb spectra were recorded over time at 25° C. The methanol or DMSO content of the solution never exceeded 0.5%. The amount of MbCO formed was determined by measuring the absorbance at 540 nm (extinction coefficient=15.4 M-1 cm-1). The MbCO concentration was plotted over time and directly related to the equivalents of CO released from the compounds. The half-life of CO release from the Re compounds at different pH's was then estimated from the graphs. Control experiments were run under identical conditions but without addition of the metal complexes. All manipulations were performed under a pure $N_2$ atmosphere in a wet box.

Synthesis of $[ReBr_2(CO)_2(MeIm)_2]$ (3)

100 mg of 2 (0.122 mmol) were suspended in 15 ml of DME and 32 mg of N-methylimidazole (MeIm, 3 eq.) were added. The mixture was heated to 60° C. for 3.5 h and stopped when the red suspension had become a yellow solution and a yellow precipitate had formed. The mixture was filtered while still hot. A bright yellow solid of 3 was collected, dried in vacuo and recrystallized from a $CH_2Cl_2$/hexane mixture giving dark red crystals. Yield: 49 mg, 71%. Anal. Calc. for $C_{10}H_{12}Br_2N_4O_2Re$ (566.2): C, 21.21%; H, 2.14%; N, 9.89%. Found: C, 21.89%; H, 2.32%; N, 9.64%. I.r. (solid state, KBr, cm$^{-1}$): $v_{C\equiv O}$ 1982, 1825. Single crystals suitable for x-ray diffraction were grown by slow diffusion of hexane into a $CH_2Cl_2$ solution of the compound.

Synthesis of $[ReBr_2(CO)_2(BzIm)_2]$ (4)

100 mg of 2 (0.122 mmol) were suspended in 15 ml of DME and 46 mg of benzimidazole (BzIm, 3 eq.) were added. The mixture was heated to 60° C. for 3.5 h and stopped when the red suspension had become a yellow solution and a yellow precipitate had formed. The mixture was filtered while still hot. A bright yellow solid of 4 was collected and dried in vacuo. The crude product was purified by loading a $CH_3OH$ solution of 4 onto a chromatofix C18 filter. This was washed with a 15% $CH_3OH$ solution in water and then extracted with $CH_3OH$. Yield: 39 mg, 50%. Anal. Calc. for $C_{16}H_{12}Br_2N_4O_2Re$ (638.3): C, 30.11%; H, 1.89%; N, 8.78%. Found: C, 29.99%; H, 1.82%; N, 8.47%. I.r. (solid state, KBr, cm$^{-1}$): $v_{C\equiv O}$ 1992, 1833. Single crystals suitable for x-ray diffraction were grown by slow diffusion of hexane into a $CH_2Cl_2$ solution of the compound giving dark red crystals.

Synthesis of $[ReBr_2(CO)_2(4\text{-pic})_2]$ (5)

100 mg of 2 (0.122 mmol) were suspended in 10 ml of DME and ca. 10 eq. 4-methylpyridine (4-pic, 100 µl) were added. After stirring overnight, a brownish precipitate was filtered off and dried in vacuo. The crude product was recrystallized from a $CH_2Cl_2$/hexane mixture giving dark red crystals of 5 which were found suitable for x-ray diffraction. Yield: 50 mg, 70%. Anal. Calc. for $C_{14}H_{14}Br_2N_2O_2Re$ (588.3): C, 28.58%; H, 2.40%; N, 4.76%. Found: C, 28.39%; H, 2.69%; N, 4.88%. I.r. (solid state, KBr, cm$^{-1}$): $v_{C\equiv O}$ 1992, 1830.

Synthesis of $[Et_4N][ReBr_2(CO)_2(4\text{-picoline amine})_2]$ (15)

100 mg of 2 (0.122 mmol) were suspended in 15 ml of DME and 39 mg of 4-picoline amine (3 eq.) were added. The mixture was stirred at room temperature for 48 h. A brown precipitate formed the was filtered. A brown solid of 15 was collected and dried in vacuo. Yield: 50 mg, 55%. $^1$H-NMR spectrum (in DMSO-d6): 8.64 (doublet, 2H), 7.47 (doublet, 2H), 4.08 (singlet, 2H). CV (in DMF, 0.1 M TBAPF$_6$ as electrolyte): Re$^I$-Re$^{II}$ couple at 0V vs Ag/AgCl. Fully reversible. I.r. (solid state, KBr, cm$^{-1}$): $v_{C\equiv O}$ 1875, 1776.

Synthesis of ReBr$_2$(CO)$_2$(4,4'-bipy)] (16)

50 mg of 2 (0.061 mmol) were suspended in 5 ml of DME and 20 mg of 4,4'-bipyridine (4,4'-bipy, 0.12 mmol, 2 eq.) were added. The suspension was heated to 60° C. for 3.5 h and stopped when the red suspension had become a deep red solution. The mixture was allowed to cool to room temperature and then filtered. The dark red solution was dried in vacuo leaving 16 as a dark red solid. The crude product was recrystallized from a $CH_2Cl_2$/hexane mixture. This procedure lead to single X-ray quality crystals of 16 and, due to decomposition of the product, a dark precipitate. Crystals of 16 were separated from the dark powder and dried in vacuo. Yield: 8 mg, 22%. Anal. Calc. for $C_{22}H_{16}Br_2N_4O_2Re$ (714.4): C, 36.99%; H 2.26%, N 7.84%. Found: C 36.90%, H 2.33%, N 7.49%. I.r. (solid state, KBr, cm$^{-1}$): $v_{C\equiv O}$ 1983, 1830. MS (ESI$^+$): m/z 715.6, i.e [M+1]$^+$, calculated 715.4.

Synthesis of $(Et_4N)_2[Re_2Br_6(CO)_4(pyz)]$ (17)

50 mg of 2 (0.061 mmol) were suspended in 7 ml of DME and 15 mg of pyrazine (pyz, 0.19 mmol, 3 eq.) were added. The mixture was heated to 60° C., allowed to react for 3.5 h and then filtered while still hot. A highly electrostatically charged brown solid of 17 was collected and dried in vacuo. Yield: 35 mg, 88%. Anal. Calc. for $C_{24}H_{44}Br_6N_4O_4Re_2$ (1304.5): C, 22.10%; H, 3.40%; N, 4.29%. Found: C, 22.89%; H, 3.36%; N, 4.12%. I.r. (solid state, KBr, cm$^{-1}$): $v_{C\equiv O}$ 1984, 1858. MS (ESI): m/z 964.1, i.e [M-Br]$^-$, calculated 964.06. Single crystals suitable for X-ray diffraction were grown by slow diffusion of hexane into a $CH_2Cl_2$ solution of the compound.

Synthesis (Et$_4$N)$_2$[Re$_2$Br$_6$(CO)$_4$(pym)] (18)

50 mg of 2 (0.061 mmol) were suspended in 7 ml of DME and 15 mg of pyrimidine (pym, 0.19 mmol, 3 eq.) were added. The mixture was heated to 60° C. and allowed to react for 3.5 h. The solution was allowed to cool to room temperature and then filtered. The solid, identified as a mixture of 2, 18 and salts was discarded. The solution was dried in vacuo giving an orange-brown powder of 18 which was recrystallized from a CH$_2$Cl$_2$/hexane mixture giving red-orange needles. Yield: 20 mg, 50%. Anal. Calc. for C$_{24}$H$_{44}$Br$_6$N$_4$O$_4$Re$_2$ (1304.5): C, 22.10%; H, 3.40%; N, 4.29%. Found: C, 22.61%; H, 3.73%; N, 4.69%. I.r. (solid state, KBr, cm$^{-1}$): $v_{C\equiv O}$ 1985, 1844. MS (ESI$^-$): m/z 964.1, i.e [M-Br]$^-$, calculated 964.06. Attempts to obtain single crystals suitable for X-ray diffraction always gave twinned red-orange needles of poor quality.

Synthesis of (Et$_4$N)$_2$[Re$_2$Br$_6$(CO)$_4$(Br-pym)] (19)

The same procedure for the synthesis of 18 was employed but using 5-Br-pyrimidine instead. Yield: 26 mg, 63%. Anal. Calc. for C$_{24}$H$_{43}$Br$_7$N$_4$O$_4$Re$_2$ (1383.4): C, 20.84%; H, 3.13%; N, 4.05%. Found: C, 21.16%; H, 3.45%; N, 4.12%. I.r. (solid state, KBr, cm$^{-1}$): $v_{C\equiv O}$ 1984, 1854. MS (ESI): m/z 1042.5, i.e [M-Br]$_-$, calculated 1043. Attempts to obtain single crystals suitable for X-ray diffraction always gave twinned red-orange needles of poor quality.

Synthesis of (Et$_4$N)[ReBr$_3$(CO)$_2$(pyd)] (20)

50 mg of 2 (0.061 mmol) and 2.5 mg of pyridazine (pyd, 0.031 mmol, 0.5 eq.) were suspended in 5 ml of DME. The mixture was heated to 60° C. and allowed to react for 5 h. The solution was allowed to cool for a few minutes and then filtered while still warm. The red-orange solid was identified as unreacted 2. The solution was dried in vacuo giving an orange-brown powder of 9 which was recrystallized from a CH$_2$Cl$_2$/hexane mixture giving yellow plates which were found suitable for X-ray diffraction. Yield: 10 mg, 25%. Anal. Calc. for C$_{14}$H$_{24}$Br$_3$N$_3$O$_2$Re (692.3): C, 24.29%; H, 3.49%; N 6.07%. Found: C, 23.99%; H, 3.52%; N, 6.20%. I.r. (solid state, KBr, cm$^{-1}$): $v_{C\equiv O}$ 1984, 1858. MS (ESI$^-$): m/z 562.8, i.e [M]$^-$, calculated 562.0.

Synthesis of B$_{12}$-CORM-2

Cyanocobalamin (B$_{12}$, 10 mg, 7.4 □mol) and 2 (10 mg, 12 □mol) were added as solids to round bottom flask. Methanol (6 mL) was added, stirring began and then the flask was lowered into an oil bath preheated to 50° C. The temperature was then lowered to 40° C. within 1 h. After 1.5 h HPLC analysis showed a single B$_{12}$ derivative. Heating was stopped and the solvent removed under reduced pressure. The resulting red powder was washed several times with CH$_2$Cl$_2$ (ca. 1.7 eq. of [Et$_4$N]Br was thus recovered) and then acetone until washings were clear. Compound B$_{12}$-CORM-2 was thus obtained as a red microcrystalline powder. Yield: 12.8 mg, 98%. HPLC analysis showed a single peak with a retention time of 22 min. Analytical data for B$_{12}$-CORM-2: ESI-MS analysis (positive mode) gave peaks at 1758.4 m/z [M+H$^+$]$^+$ and 879.8 m/z [M+H$^+$]$^{2+}$. I.r. (solid state, KBr, cm$^{-1}$): $v_{C\equiv N}$ 2184, □$_{C\equiv O}$ 1989, 1839.

Synthesis of B$_{12}$-CORM-4

Cyanocobalamin (400 mg, 0.3 mmol) was dissolved in 10 mL of anhydrous DMSO and carbonyldiimidazole (CDI, 1 g, 6.2 mmol) was added. The solution was stirred and heated to 60° C. for 12 h. The solution was allowed to cool to room temperature (RT) and then slowly added to a rapidly stirring mixture of 300 mL 1:1 diethyl ether:chloroform. The red precipitate was collected by vacuum filtration, washed with 50 mL of acetone and vacuum dried. Yield: 395 mg. This product was not purified but used directly for the next reaction. 100 mg of the activated vitamin was dissolved in 5 mL of anhydrous DMSO and 4-picolylamine (100 μl, 1 mmol) was added. The solution was stirred at RT for 30 min and then slowly added to a rapidly stirring mixture of 150 mL 1:1 diethyl ether:chloroform. The red precipitate was collected by vacuum filtration, washed with 30 mL of acetone and vacuum dried. Yield: 109 mg. This precipitate consists of a mixture of products. The cyanocobalamin derivative with HPLC retention time of 15 min was purified by HPLC. Yield 45 mg. This derivative was reacted with 2 as described for B$_{12}$-CORM-2. Compound B$_{12}$-CORM-4 was obtained as a red microcrystalline powder. Yield: 4.9 mg, 95. HPLC analysis showed a single peak with a retention time of 25 min. Analytical data for B$_{12}$-CORM-4: ESI-MS analysis (positive mode) gave peaks at 1893.4 m/z [M+H$^+$]$^+$ and 946.8 m/z [M+H$^+$]$^{2+}$. I.r. (solid state, KBr, cm$^{-1}$): $v_{C\equiv N}$ 2184, □$_{C\equiv O}$ 1989, 1839.

Synthesis of Complexes

A summary of the reactions of compound 2 with different mono-, bi- and tridentate ligands is given in the graphic schemes below. As previously shown, complex 2 reacts well with monodentate nitrogen containing aromatic ligands (Zobi et al., Inorg. Chem. 2009, 48, 8965-8970). Thus, the reaction with N-methylimidazole (MeIm), 4-picoline (4-pic) or benzimidazole (BzIm) gave the corresponding cis-trans-[Re$^{II}$(CO)$_2$Br$_2$L2] complex (compound 3 with L=MeIm, compound 4 with L=BzIm, compound 5 with L=4-pic). The direct substitution reaction of 2 with this type of ligands allowed to isolate 3, 4 and 5 in a short time and in good isolated yields (>50%). With the exception of 3, which was found to be hydroscopic and slowly decomposed over time, 4 and 5 appear indefinitely stable as solids under aerobic conditions.

Scheme 1. Synthesis of Rhenium complexes 3 to 15.

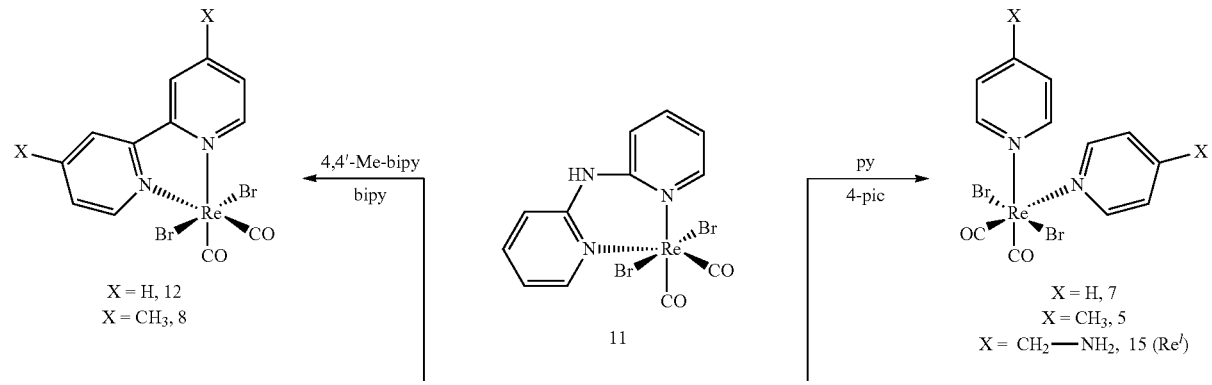

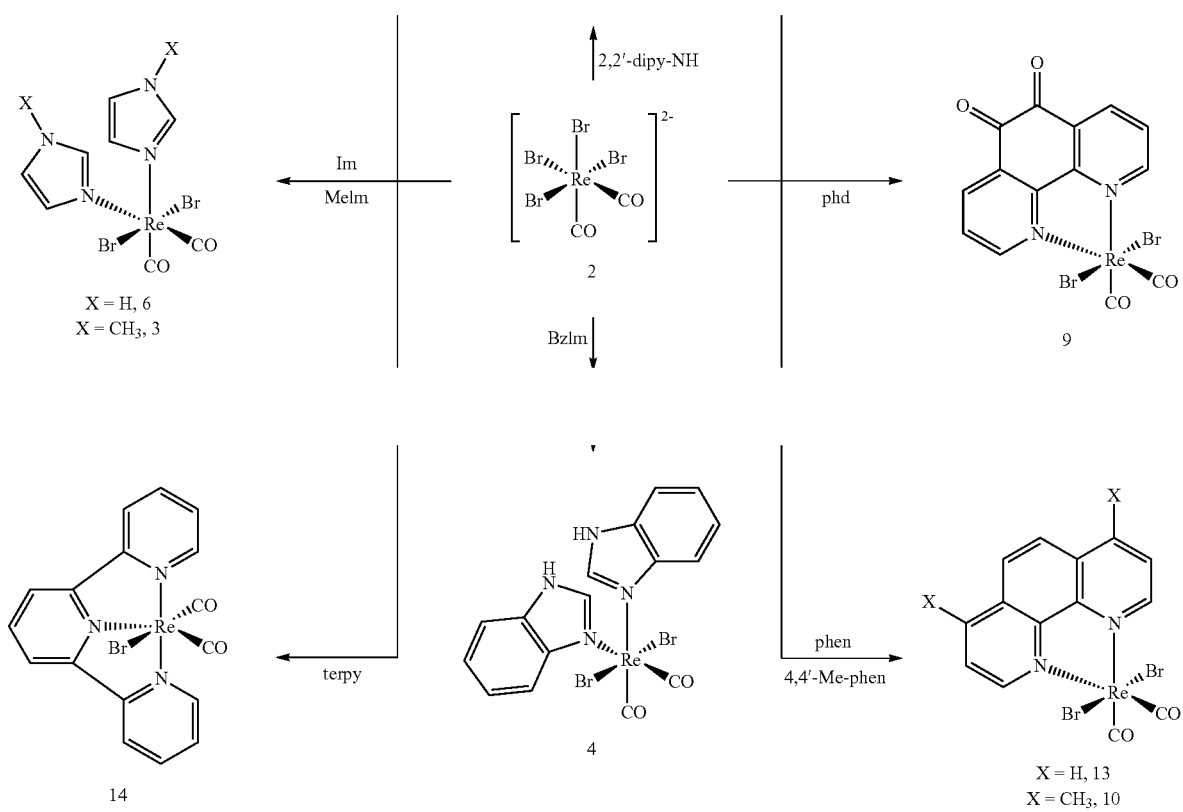
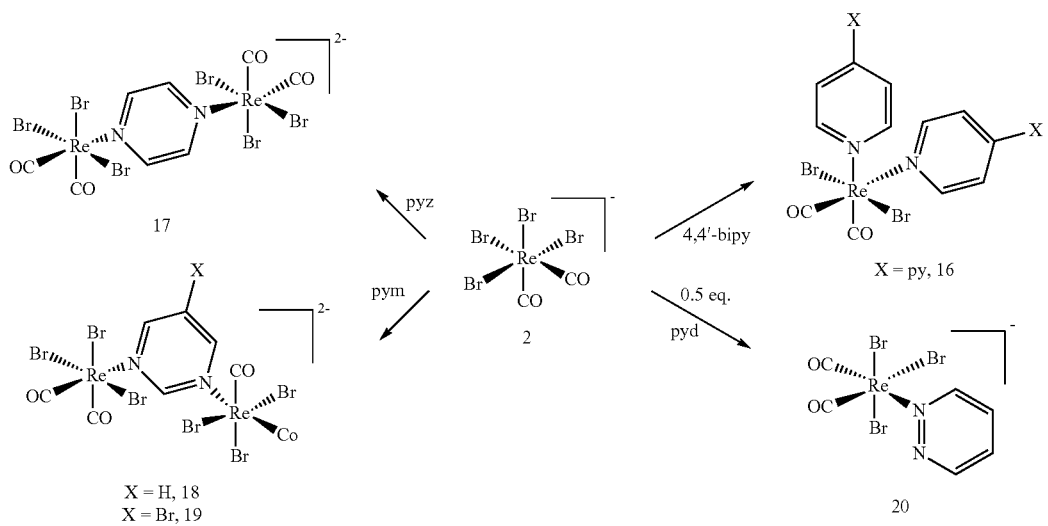
Scheme 2. Synthesis of Rhenium complexes 16 to 20.

Synthesis of B$_{12}$—CORM-2 and B$_{12}$—CORM-4.

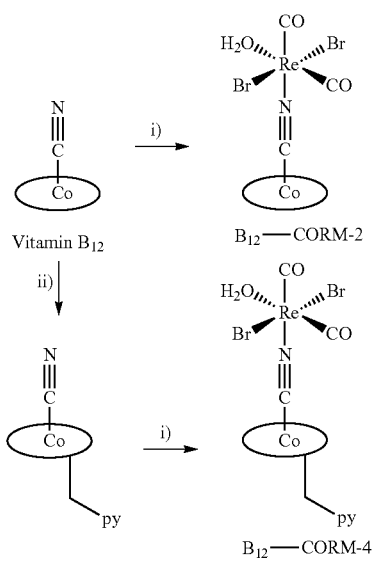

Reagents and conditions: i) [Et$_4$N]$_2$[Re"Br$_4$(CO)$_2$], methanol/water, 1.5 h, 40-50° C.; ii) CDI, DMSO, 12 h, 60° C. followed by 4-picolylamine, 0.5 h, RT.

The cyanocobalamin (B$_{12}$) derivatives of 17-electrons rhenium dicarbonyl species shown in Scheme 3 are a second generation of Re$^{II}$-based CO-RMs. They show several improved features over the original family. The derivatives: a) are fully water soluble and biocompatible, b) show improved stability in aqueous aerobic media over the metal complex alone, c) are non-toxic towards cultured cardiomyocytes, d) protect these cells against ischemia-reperfusion injury and e) after CO release, in water under aerobic conditions, the rhenium complex is oxidized to ReO$_4^-$ which is among the least toxic of all of the rare inorganic compounds.

Complexes 3-5 are soluble in common organic solvents like methanol, CH$_2$Cl$_2$, acetonitrile or DMSO and even under aerobic conditions are stable for days. X-ray quality crystals of 3, 4 and 5 could be grown from CH$_2$Cl$_2$. In all cases the ligands L substituted the two bromides trans to the CO's resulting in [Re$^{II}$(CO)$_2$Br$_2$L2] complexes with a cis-trans-cis arrangement of the ligands. Since the cis arrangement of the two COs is the only structural compulsion, other isomers are expected as well. A common feature of the compounds 3-5 is the bending of the two trans bromides away from the CO's with an average Br—Re—Br angle of 171.5°. Bond lengths and angles of 3 and 5 were found similar to the related imidazole and pyridine complexes cis-trans-[Re$^{II}$(CO)$_2$Br$_2$(Im)$_2$] (6) and cis-trans-[Re$^{II}$(CO)$_2$Br$_2$(py)$_2$] (7) previously described (Zobi et al., Inorg. Chem. 2009, 48, 8965-8970.). When reacted with others heterocyclic aromatic ligands like THF or thiophene, 2 was always recovered unreacted indicating that, under similar experimental conditions, these ligands are not strong enough to replace the bound bromides even if present in large excess. While the MeIm and 4-pic ligands were mainly selected in order to provide data for comparison to the Im and py adducts 6 and 7, BzIm was also selected as a simple model for the interaction of 2 with purine bases. In 4 the two BzIm ligands are found in a head-to-tail (HT) conformation. Our previous results of the interaction of DNA bases with the fac-[Re$^I$(CO)$_3$(H$_2$O)$_3$]$^+$ complex have shown that neither hydrogen bonding interactions nor steric factors are important in determining the orientation of the bases around the Re$^I$ core. The bases were found to be able to freely rotate around the metal center and we have shown that the different head-to-head (HH) or HT conformers observed in the solid state structures of the adducts are a result of packing effects (Zobi et al., Inorg. Chem. 2004, 43, 2087-2096). The BzIm and other purine-type ligands are expected to be able to freely rotate around the cis-[Re$^{II}$(CO)$_2$]$^{2+}$ core. Thus, the HT conformer observed in the solid state structure of 4 is unlikely to be the predominant form in solution.

Reaction of 2 with bidentate bipyridine or phenantroline type ligands proceeded smoothly with no reduction of the Re$^{II}$ center. Thus, 4,4'-dimethyl-2,2'-bipyridine (4,4'-Mebipy), 1,10-phenanthroline-5,6-dione (phd), 4,7-dimethyl-1,10-phenanthroline (4,7-Mephen) and 2,2'-dipyridylamine (2,2'-dipy-NH) gave the corresponding cis-trans-[Re$^{II}$(CO)$_2$Br$_2$N∩N] complexes (8 with N∩N=4,4'-Mebipy, 9 with N∩N=phd, 10 with N∩N=4,7-Mephen and 11 with N∩N=2,2'-dipy-NH; see scheme 2).

TABLE 1

Spectroscopic and electrochemical properties of complexes 2-14.

| Complex | $v_{CO}$ (cm$^{-1}$)$^a$ | E½, (mV)$^b$ | λ$_{max}$ (nm)$^c$ |
| --- | --- | --- | --- |
| [Re(CO)$_2$Br$_4$]$^{2-}$ (2)$^1$ | 1972, 1796 | −120 | 412 |
| [Re(CO)$_2$Br$_2$(MeIm)$_2$] (3) | 1982, 1825 | dec. | 418 |
| [Re(CO)$_2$Br$_2$(BzIm)$_2$] (4) | 1992, 1833 | −195 | 418 |
| [Re(CO)$_2$Br$_2$(4-pic)$_2$] (5) | 1992, 1830 | −90 | 423 |
| [Re(CO)$_2$Br$_2$(Im)$_2$] (6)$^1$ | 1988, 1826 | dec. | 418 |
| [Re(CO)$_2$Br$_2$(py)$_2$] (7)$^1$ | 1990, 1825 | −76 | 425 |
| [Et$_4$N][Re(CO)$_2$Br$_2$(4-picolineamine)$_2$] (15) | 1875, 1776 | 0 | |

$^a$KBr.
$^b$Potentials are reported vs. Ag/AgCl reference electrode in CH$_3$OH for 2-7 and with 0.1M TBAPF$_6$ as an electrolyte. All processes are one electron and refer to the Re$^{II}$ → Re$^I$ reduction for 2-7 and to Re$^I$ → Re$^{II}$ oxidation for 15 in DMF and in CH$_2$Cl$_2$ for all others.

TABLE 2

Crystallographic data for compounds 3-5.

| Comp. | 3 | 4 | 5 |
| --- | --- | --- | --- |
| Formula | C$_{10}$H$_{12}$Br$_2$—N$_4$O$_2$Re | C$_{16}$H$_{12}$Br$_2$—N$_4$O$_2$Re | C$_{14}$H$_{14}$Br$_2$—N$_2$O$_2$Re |
| FW | 566.26 | 638.32 | 588.29 |
| T, K | 183 (2) | 183 (2) | 183 (2) |
| space group | C2/c | C2/c | Pcca |
| crystal system | monoclinic | monoclinic | orthorhombic |
| Z | 8 | 4 | 4 |
| a, Å | 30.1515 (16) | 10.6383 (4) | 13.33059 (15) |
| b, Å | 7.62680 (19) | 12.4396 (3) | 8.38345 (9) |
| c, Å | 15.1080 (7) | 13.7647 (4) | 15.52929 (19) |
| β, deg | 119.758 (7) | 99.358 (3) | 90 |

TABLE 2-continued

Crystallographic data for compounds 3-5.

| Comp. | 3 | 4 | 5 |
|---|---|---|---|
| V, Å$^3$ | 3016.1 (2) | 1797.34 (9) | 1735.50 (3) |
| $d_{calc}$, g/cm$^3$ | 2.494 | 2.359 | 2.252 |
| R1(wR2)$^a$ | 0.0319 (0.0569) | 0.0253 (0.0670) | 0.0200 (0.0640) |
| largest diff. peak/hole (e Å$^{-3}$) | 1.639 and −0.894 | 1.170 and −0.842 | 0.848 and −1.208 |

$^a$[I > 2sigma(I)]

Example 2

Biological Properties

CO-Releasing Properties of cis-trans-[Re$^{II}$(CO)$_2$Br$_2$L$_2$]$^n$ Complexes.

Figure 2:
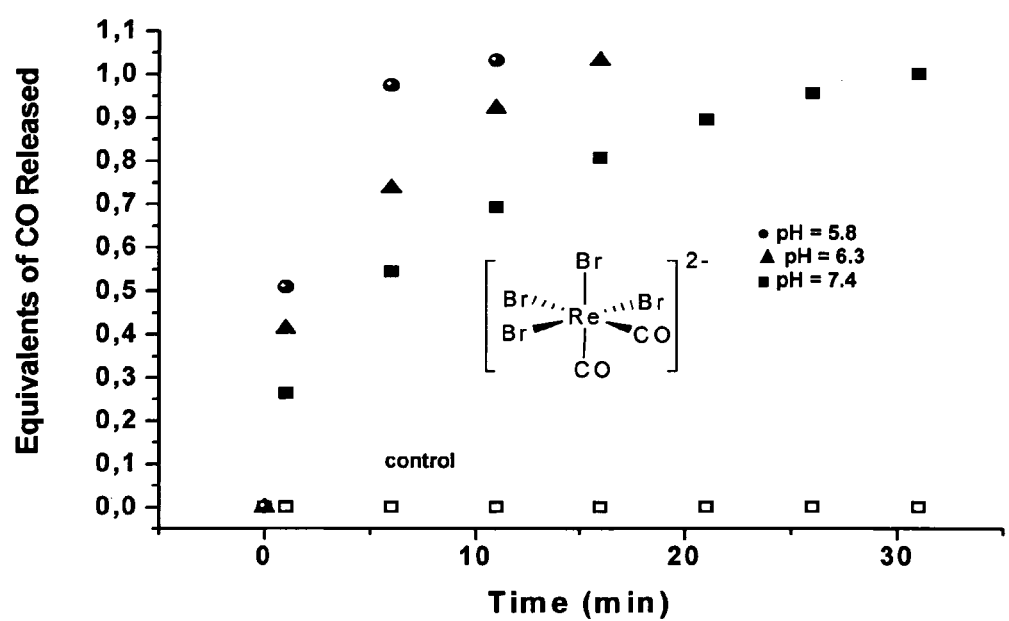
FIGS. 2 to 7 graphically represent the results of the pH-dependent rate of CO release of different cis-trans-[$Re^{II}(CO)_2Br_2L2$]$^n$ complexes under conditions of 30 μM Mb (myoglobin), 25° C., 0.1 M phosphate buffer, pH 7.4 (●), 6.3 (▲), 5.8 (■).
Figure 3:
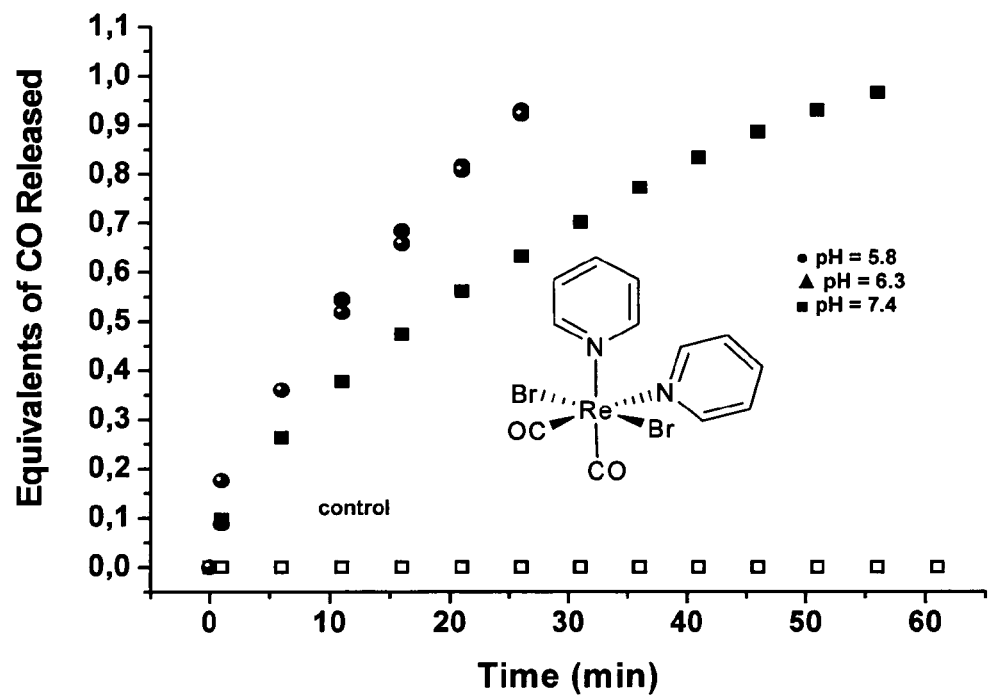
Figure 4:
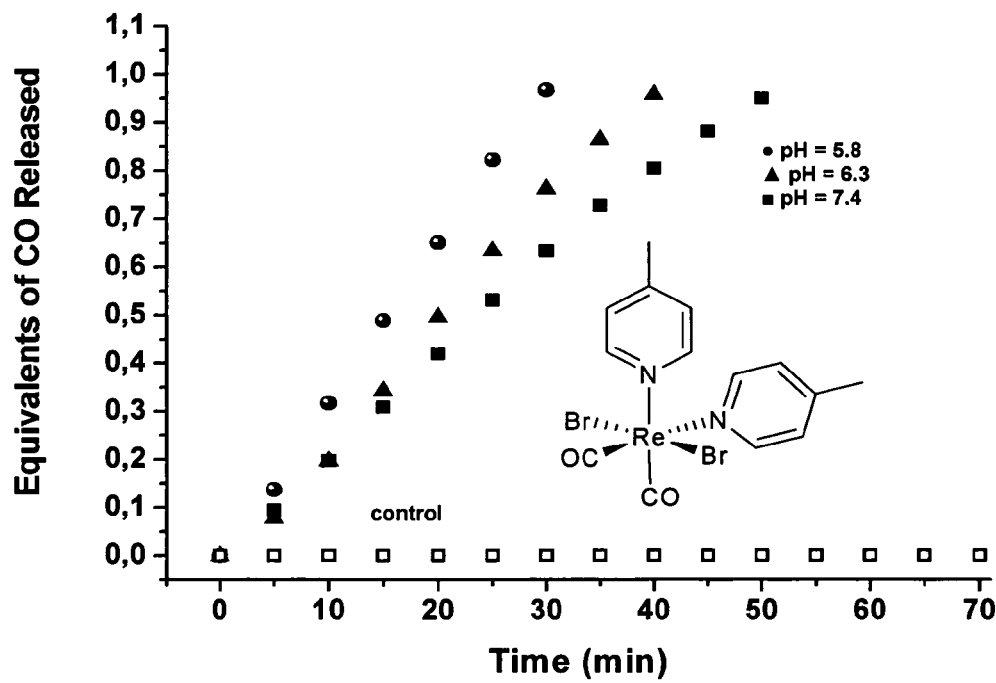

The carbon monoxide releasing properties of cis-trans-[Re$^{II}$(CO)$_2$Br$_2$L2]$^n$ complexes were evaluated by the myoglobin assay (FIG. 2A). This assay has been shown to be a reliable method for assessing the amount and kinetic of CO liberation from CO-releasing molecules (Clark et al., Circ. Res. 2003, 93, e2-8, Motterlini et al., Circ. Res. 2002, 90, E17-24, Motterlini et al., Curr. Pharm. Des. 2003, 9, 2525-2539). In these experiments an aliquot of a freshly prepared concentrated solution of the [Re$^{II}$(CO)$_2$Br$_2$L2]$^n$ complex was added to a buffered solution of horse skeletal myoglobin (Mb) freshly reduced with excess sodium dithionite under N$_2$. With the exception of compound 2 all complexes tested are insoluble in water. However, stock solutions of 2 in water were found to generate an inactive form of the complex due to the accelerated CO release from this compound. Thus, solutions of 2 were prepared in methanol while stock solutions of compounds 3-13 were prepared in DMSO. The final methanol or DMSO content of the buffered aqueous solution never exceeded 0.5%. The conversion of Mb to carbon monoxide myoglobin (MbCO) was followed over time by measuring the changes in the absorption spectra of the Q band region of this protein at pH 7.4, 6.3 and 5.8 after addition of the Re$^{II}$ complex. The maximal absorption peak of Mb at 560 nm was rapidly converted over time to spectrum of MbCO, with two maximal absorption peaks at 540 and 578, respectively. A typical spectrum is shown in FIG. 1.

Only compounds bearing monodentate ligands (i.e. compounds 2-7 in Scheme 1, compounds 16-20 in Scheme 2 and B$_{12}$-CORM-2 and B$_{12}$-CORM-4. in Scheme 3) elicited the spectral changes associated with CO release. The amount of MbCO formed over time after addition of the Re complex to the Mb solution was calculated according to the known extinction coefficients. The MbCO concentration was directly related to the equivalents of CO released from the compounds and these were plotted as a function of time. FIGS. 2 to 7 show the graphic representation of results relating to the pH-dependent rate of CO release of different cis-trans-[Re$^{II}$(CO)$_2$Br$_2$L$_2$]$^n$ complexes. The half-lives (t$_{1/2}$) of CO release from the Re$^{II}$ complexes at different pH's were estimated from these graphs and are listed in table 3.

TABLE 3

Half-lifes (t½, min, 25° C.)a for the release of 1 equivalent of CO by cis-[Re$^{II}$(CO)$_2$Br$_2$L$_2$]$^n$ complexes at different pH's.$^b$

| Complex | t$_{1/2}$ at pH 5.8 | t$_{1/2}$ at pH 6.3 | t$_{1/2}$ at pH 7.4 |
|---|---|---|---|
| [Re(CO)$_2$Br$_4$]$^{2-}$ (2) | 1.0 | 2.5 | 5.7 |
| [Re(CO)$_2$Br$_2$(MeIm)$_2$] (3) | 19.9 | 27.0 | 40.7 |
| [Re(CO)$_2$Br$_2$(BzIm)$_2$] (4) | 8.4 | 12.3 | 14.0 |
| [Re(CO)$_2$Br$_2$(4-pic)$_2$] (5) | 15.2 | 20.3 | 23.6 |
| [Re(CO)$_2$Br$_2$(Im)$_2$] (6) | 29.8 | 41.3 | 42.3 |
| [Re(CO)$_2$Br$_2$(py)$_2$] (7) | 9.7 | 10.2 | 17.2 |
| [Et$_4$N][Re(CO)$_2$Br$_2$(4 picoline amine)$_2$] (15) | Not yet measured | Not yet measured | ca. 20 |

Figure 5:
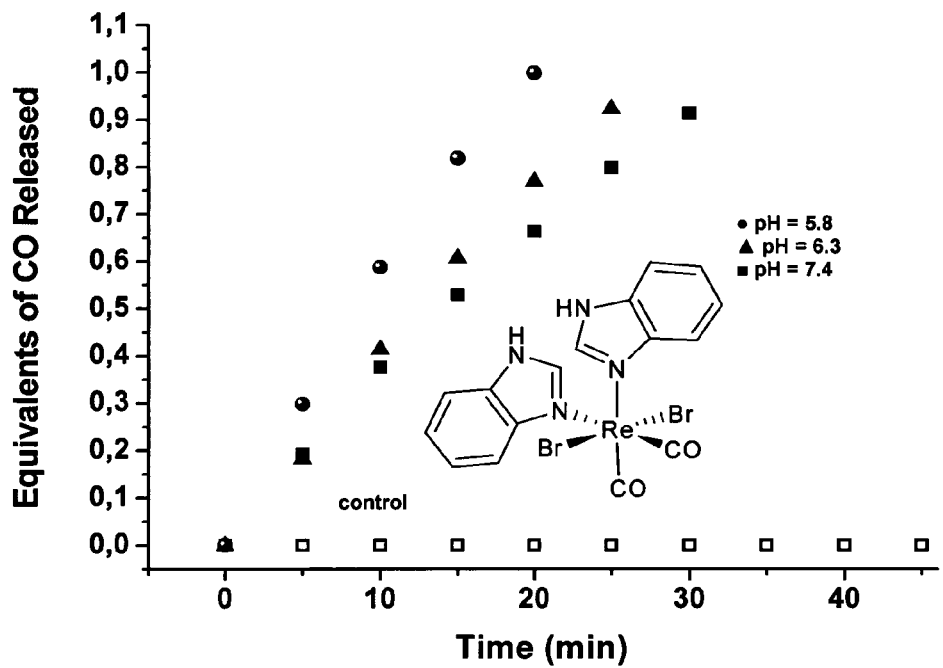
Figure 6:
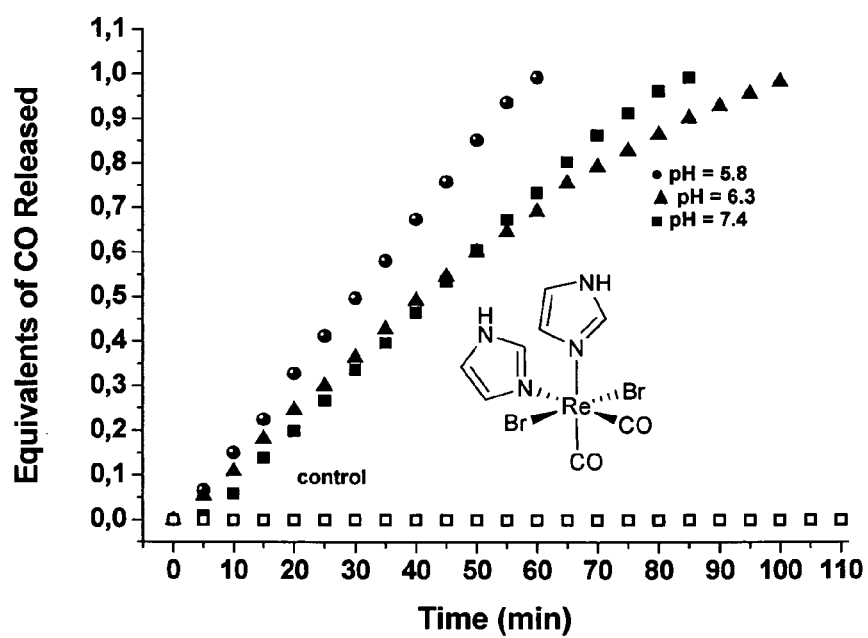
Figure 7:
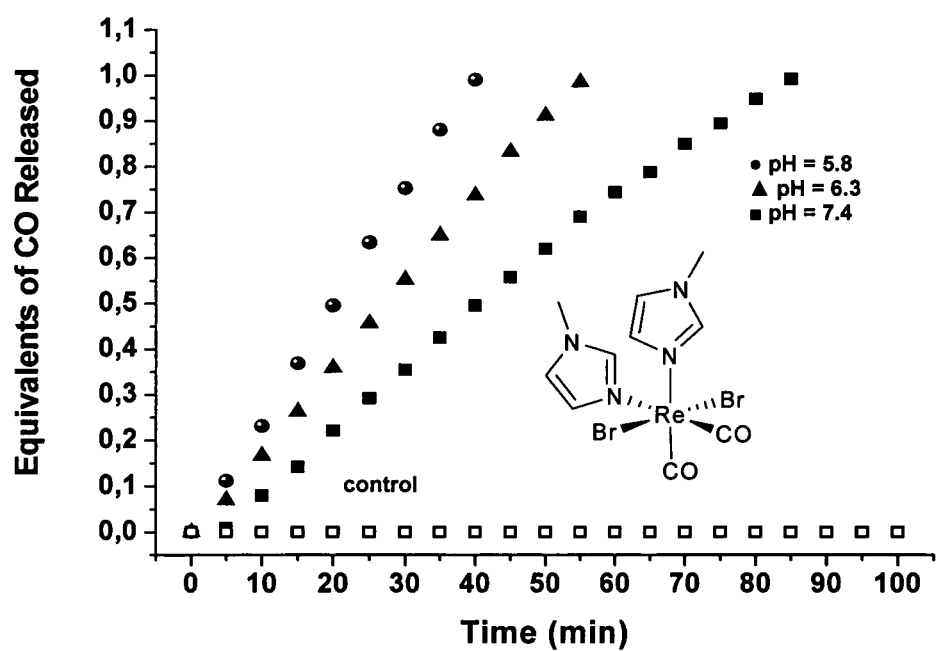

$^a$Half-lives (t$_{1/2}$) were estimated from the fitted curves shown in FIG. 5.
$^b$0.1M phosphate buffer.
$^c$n.d. = not determined; i.e. the complex does not release CO.

When the experiments were performed under conditions of a limiting amount of the metal complexes, taking into account the molar extinction coefficient of MbCO, it was found that approximately 1 mol of CO was released per mole of the corresponding —[Re$^{II}$(CO)$_2$Br$_2$L2]$^n$ species. Thus, only one CO ligand is liberated from the metal complexes 2-7. The CO detection via this assay proceeded as expected with three isosbestic points at 552, 567 and 587 nm clearly visible in the spectrum (see FIG. 1). As described above, changes in the spectrum are indicative of the conversion of Mb to MbCO.

However, after full CO saturation of Mb the molar absorptivity in the Q band region of MbCO increased over time beyond the expected calculated value. All three isosbestic points were lost. There was no further spectral change in terms of the position of the maximal absorption peaks at 540 and 578, but only an apparent increase in their molar absorptivity. This was true for all [Re$^{II}$(CO)$_2$Br$_2$L2]$^n$ species tested and for all pH's and for complex 15. The rate of CO loss from compounds 2-7 was found to be pH-dependent with half lives (t$_{1/2}$) under physiological conditions (pH 7.4) varying from about 6 (for 2) to 43 min (for 6, table 3). At lower pH values the time required to fully saturate Mb with CO liberated from the metal complexes gradually decreased. This was generally true for all compounds except for [Re(CO)$_2$Br$_2$(Im)$_2$] (6) and [Re(CO)$_2$Br$_2$(py)$_2$] (7), where only small difference were detected between pH 7.4 and 6.3 and between pH 6.3 and 5.8 respectively (table 3). Complex 2 was found to be the most rapid CO-releasing molecule (CORM) in all cases while the imidazole adducts were the slowest. The overall order for the rate of CO release for the compounds tested is: 2>4≈7>5>3≈6. At pH 7.4 and at 25° C. saturation of Mb with CO liberated from compound 2 was reached within 30 min (t$_{1/2}$=5.7 min). This value is comparable to that of the fac-[RuCl(glycinato)(CO)$_3$] complex (CORM-3) whose t$_{1/2}$ at pH 7.4 and at 37° C. has been reported to be about 1 min.

The above results prove that for the compounds of the invention, the rate of CO release can be controlled by the appropriate choice of ligands. Thus, fine tuning of the coordination sphere allows for the design of inventive compounds with specific rates of CO loss.

Cytoprotective Effects of $B_{12}$-CORMs.

$B_{12}$-CORM-2 and 4 (Scheme 3) were tested for their cytotoxic and their cytoprotective effects using the neonatal rat cardiomyocyte (NRC) cell-based model of ischemia-reperfusion injury (I/R) as previously described (Zobi et al., Inorg. Chem. 2010, 49, 7313-7322). The membrane-impermeable ReII-CORMs studied so far were non-toxic in the micromolar concentration range. To test for the possible uptake of $B_{12}$-CO-RMs by cells incubation of NRCs with 30 μM of $B_{12}$-CORM-2 and 4 was performed and cell culture medium samples were collected over 180 min of incubation. Atomic absorption spectroscopy (AAS) measurements showed that the rhenium concentration in the medium supplemented with $B_{12}$-CORM-2 and $B_{12}$-CORM-4 did not change over time. This observation implies that complexes (or the dissociated Re fragment) did not enter the cells through the cell surface membrane during a 3 h incubation period (data not shown). The fraction of dead cells tended to decrease in the presence of CORMs, but, due to the high variability, the differences were not statistically significant (2.7±1.7% in control vs 1.1±0.3 and 1.0±0.2 in the presence of $B_{12}$-CORM-2 and $B_{12}$-CORM-4 respectively).

Figure 8:
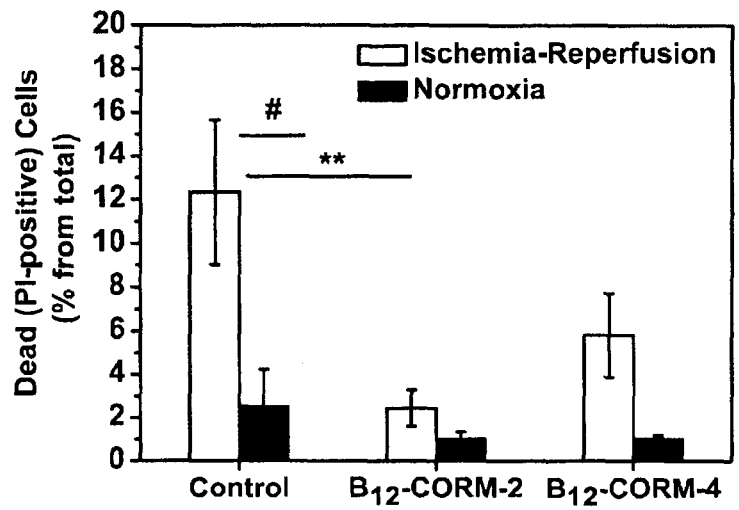
FIG. 8. Cytoprotective effects of conjugates $B_{12}$-CORM-2 and $B_{12}$CO-RM-4 (30 μM) against "ischemia-reperfusion" injury (I/R). Cell damage in neonatal rat ventricular cardiomyocytes (NRCs) after 16 h of ischemia (hypoxia, aglycemia, and acidosis). CO-RMS or the aliquot of solvent (DMSO) were added to the cell culture medium at the onset of reperfusion period of 9 h at 30 μM concentration. Bars indicate the % of PI-positive (dead) cells. ** denotes p<0.01 when I/R $B_{12}$-CORM-2-treated cells are compared to I/R control. # denotes p<0.05 when normoxic cells are compared with I/R control.

Exposure of the NRCs to the conditions mimicking ischemia-reperfusion resulted in a 5-fold increase in the number of dead cells (control in FIG. 8). Administration of 30 μM $B_{12}$-CORM-2 at the "onset of reperfusion" nearly prevented cell mortality (cell death was reduce by ca. 80% as compared to control) whereas 30 μM $B_{12}$-CORM-4 reduced cell death by ca. 50%. Thus, $B_{12}$-CORM-2 proved to be more efficient in preventing I/R-induced cell death than $B_{12}$-CORM-4. Therefore $B_{12}$-CORM-2 was chosen for further investigation and compared to $[Et_4N]_2[Re^{II}Br_4(CO)_2]$ (2) and the cis-trans-$[Re^{II}(CO)_2Br_2(Im)_2]$ complex (6) that also exhibited substantial cytoprotective effects. (Zobi et al., Inorg. Chem. 2010, 49, 7313-7322.). All three compounds release CO in aqueous solution, albeit at different rates, and with the exception of the lipophilic 6 are well soluble in water. Under normal physiological conditions the compounds showed no cytotoxicity towards NCRs up to a tested concentration of 120 μM.

Figure 9:
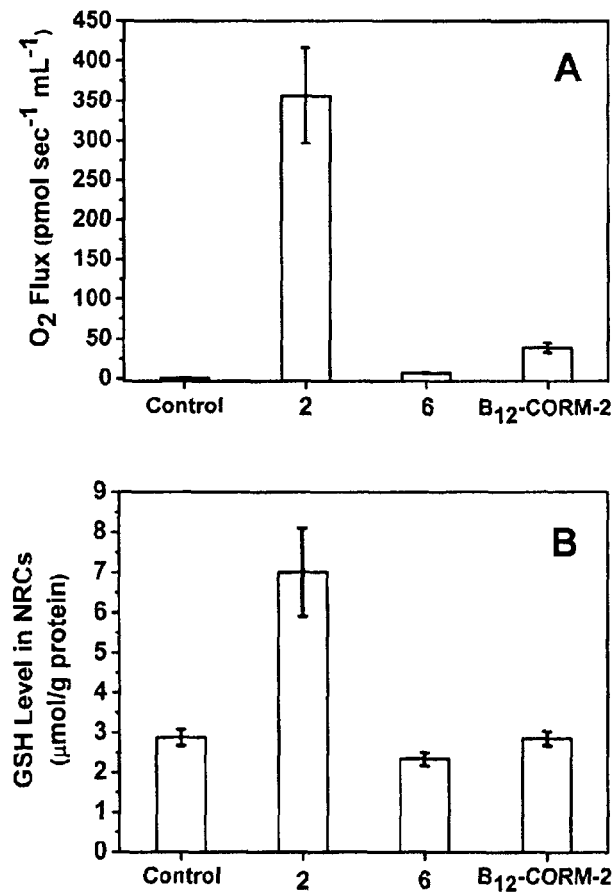
FIG. 9. Regulation of oxygen availability and the intracellular reduced glutathione content by Re-CORMs. A: Reduction in oxygen content in the incubation medium within 10 min after addition of 60 μM of 2, 6 and $B_{12}$-CORM-2; N=6-8. Given are means±SEM. B: Intracellular reduced glutathione (GSH) content in NRCs exposed to 16 h of ischemia and 10 min of reperfusion in the presence or absence of CO-RMs. N=4 Data are means±SEM.

Carbon monoxide is known to suppress respiration in different cell types by inhibiting the mitochondrial electron transfer chain and by interfering with oxygen binding. Therefore, the effect of the three selected CO-RMs on oxygen consumption by NRCs was investigated. None of the tested compounds displayed any significant effect on oxygen consumption by NRCs within the concentration range relevant for cytoprotection within 30 min of observation. The lack of effect neither depended on the rate of CO release nor on the compound solubility. Interestingly, addition of 2 and to a lesser extent of $B_{12}$-CORM-2 resulted in deoxygenation of the cell-free medium within minutes after administration. This CORM-induced deoxygenation was dose-dependent. The deoxygenation efficiency followed the kinetics of CO release (and thus the decay of the $Re(CO)_2$ fragment) and was maximal for the fast-releasing 2 compound (FIG. 9A).

Oxidative stress triggered by acute hyperoxygenation is a hallmark of reperfusion injury. Based on the findings presented in FIG. 9A selected CORMs may be viewed as oxygen scavengers which, when applied early on during reperfusion, may reduce the cellular oxidative damage. To test this hypothesis intracellular reduced glutathione (GSH) levels were determined in cells 10 min after the "onset of reperfusion" in the presence or absence of 30 μM 2, 6 and $B_{12}$-CORM-2. As shown in FIG. 9B, presence of 2 complex at reperfusion resulted in an increase in the intracellular reduced glutathione (GSH) levels reflecting its antioxidative action. (FIG. 9B). This acute antioxidative effect of 2 most likely reflects the ability of the intermediates formed upon CO release to react with oxygen forming $ReO_4^-$.

Although the molecular mechanisms of the observed cytoprotective effects of the above-mentioned CO-RMs remain unknown, their cytoprotective action may, at least in part, be attributed to the extracellular release of CO and to the de-oxygenating effect described above. Finally, our observations suggest that the protective effect of $Re^{II}$-based CO-RMs is not related to a decrease in mitochondrial respiration and secondary free radical production.

The invention claimed is:

1. A compound of formula $\{Re^{II}Br_2(CO)_2(L)_2\}^{2-}$ wherein at least one L is selected from the group consisting of water, halides, carbon monoxide, N-methyl imidazole, benzimidazole, 4-methyl pyridine, imidazole, pyridine, pyridine, Vitamin B12, and alcohol, optionally substituted by one to four R"; provided that at least one L is vitamin B12 optionally substituted by one to four R"; wherein each R" is independently selected from the group consisting alkyl, alkenyl, alkynyl, alkylidene, cycloalkyl, aryl, heteroaryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, hydroxy, halogen, trifluoromethyl, nitro, nitrile and amino optionally mono-, di- or tri- substituted by $C_{1-6}$ alkyl, $C_{1-6}$ acyl or $C_{2-7}$ alkoxycarbonyl; wherein any members of the group and/or of the R" are optionally halogenated; or a tautomer, an isomeric form, a racemate, a single enantiomer, a diastereomer or mixtures thereof, or a pharmaceutically acceptable salt; wherein the compound has a carbon monoxide release with a half-life of six minutes to an hour.

2. The compound according to claim 1 selected from the following group:

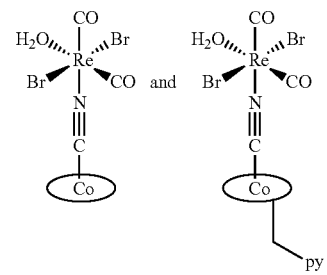

wherein py is pyrimidine and "N≡C—Co" is cyanocobalamin.

3. The compound according to claim 1 having a stereochemistry wherein the two carbon monoxides have a cis configuration, the two bromides have a trans configuration and the two remaining ligands L have a cis configuration.

4. A pharmaceutical composition comprising at least one compound according to claim 1 and optionally one or more pharmaceutically acceptable carriers and/or adjuvants.

* * * * *